(12) United States Patent
Hebeisen et al.

(10) Patent No.: US 10,766,874 B2
(45) Date of Patent: *Sep. 8, 2020

(54) MANUFACTURING PROCESS FOR TRIAZINE, PYRIMIDINE AND PYRIDINE DERIVATIVES

(71) Applicants: UNIVERSITAET BASEL, Basel (CH); PIQUR THERAPEUTICS AG, Basel (CH)

(72) Inventors: Paul Hebeisen, Basel (CH); Florent Beaufils, Bartenheim (FR); Jean-Baptiste Langlois, Sierentz (FR)

(73) Assignees: UNIVERSITAET BASEL, Basel (CH); PIQUR THERAPEUTICS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/045,427

(22) Filed: Jul. 25, 2018

(65) Prior Publication Data

US 2019/0016698 A1 Jan. 17, 2019

Related U.S. Application Data

(63) Continuation of application No. 15/304,595, filed as application No. PCT/EP2015/058493 on Apr. 20, 2015, now Pat. No. 10,100,031.

(30) Foreign Application Priority Data

Apr. 22, 2014 (EP) .................................. 14 165 418

(51) Int. Cl.
- C07D 401/04 (2006.01)
- C07D 213/127 (2006.01)
- A61K 31/5377 (2006.01)
- C07D 213/53 (2006.01)
- C07F 5/02 (2006.01)

(52) U.S. Cl.
CPC ........ *C07D 401/04* (2013.01); *A61K 31/5377* (2013.01); *C07D 213/127* (2013.01); *C07D 213/53* (2013.01); *C07F 5/025* (2013.01)

(58) Field of Classification Search
None
See application file for complete search history.

(56) References Cited

U.S. PATENT DOCUMENTS

| | | | |
|---|---|---|---|
| 4,727,145 A | 2/1988 | Press | |
| 8,217,035 B2 | 7/2012 | Burger et al. | |

FOREIGN PATENT DOCUMENTS

| | | |
|---|---|---|
| GB | 1321736.9 | 1/2014 |
| WO | WO 01/62756 A1 | 8/2001 |
| WO | WO 02/40476 A1 | 5/2002 |
| WO | WO 03/042207 A1 | 5/2003 |
| WO | WO 2007/039439 A1 | 4/2007 |
| WO | WO 2007/084786 A1 | 7/2007 |
| WO | WO 2009/027283 A1 | 3/2009 |
| WO | WO 2010/052569 A2 | 5/2010 |
| WO | WO 2010/091067 A2 | 8/2010 |
| WO | WO 2011/109932 A1 | 9/2011 |
| WO | WO 2011/110479 A1 | 9/2011 |
| WO | WO 2012/044727 A2 | 4/2012 |
| WO | WO 2012/109423 A1 | 8/2012 |
| WO | WO 2013/101974 A1 | 7/2013 |
| WO | WO 2013/107326 A1 | 7/2013 |
| WO | WO 2014/009295 A1 | 1/2014 |
| WO | WO 2014/055955 A1 | 4/2014 |
| WO | WO 2014/064058 A2 | 5/2014 |
| WO | WO 2015/086499 A1 | 6/2015 |

OTHER PUBLICATIONS

International Search Report issued in PCT/EP2015/058493, dated Aug. 31, 2015.
Gomez-Garcia et al., *Bull. Korean Chem. Soc.* 34(9):2807-2810 (2013).
Greene, Protective Groups in Organic Synthesis (1991), Chapter 7, pp. 696-926.
Jeong et al., *ChemMedChem* 7:1379-1383 (2012).
Varchi et al., *Synlett.* 4:477-480 (2001).
Chemical Abstract Services, STN Database Registry No. 1536396-22-1, entered into STN Feb. 3, 2014.
Chemical Abstract Services, STN Database Registry No. 1536391-74-8, entered into STN Feb. 3, 2014.

(Continued)

*Primary Examiner* — Kamal A Saeed
(74) *Attorney, Agent, or Firm* — Medler Ferro Woodhouse & Mills PLLC

(57) ABSTRACT

The invention relates to a method of manufacturing triazine, pyrimidine and pyridine derivatives of formula (I)

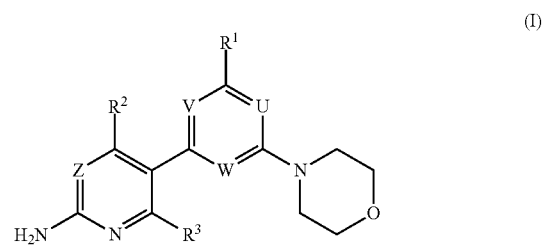

(I)

wherein U, V, W and Z are nitrogen or carbon atoms, whereby at least one of U, V and W is nitrogen, and the other substituents are defined as in the specification, by condensing a corresponding halo-triazine, pyrimidine or pyridine in a type of Suzuki coupling with a pyridyl- or pyrimidinyl-borane, wherein the amino function is protected as a formamidine. The invention further relates to suitable intermediates and methods of manufacturing of such intermediates. Furthermore the invention relates to pure 5-(4,6-dimorpholino-1,3,5-triazin-2-yl)-4-(trifluoromethyl)pyridin-2-amine in solid form.

20 Claims, 1 Drawing Sheet

(56) References Cited

OTHER PUBLICATIONS

Chemical Abstract Services, STN Database Registry No. 1536390-60-9, entered into STN Feb. 3, 2014.
Chemical Abstract Services, STN Database Registry No. 1536390-46-1, entered into STN Feb. 3, 2014.
Chemical Abstract Services, STN Database Registry No. 1482464-98-1, entered into STN Nov. 27, 2013.
Chemical Abstract Services, STN Database Registry No. 1400188-62-6, entered into STN Oct. 8, 2012.
Chemical Abstract Services, STN Database Registry No. 1400188-60-4, entered into STN Oct. 8, 2012.
Chemical Abstract Services, STN Database Registry No. 1236325-05-5, entered into STN Aug. 17, 2010.
Chemical Abstract Services, STN Database Registry No. 883052-76-4, entered into STN May 5, 2006.
Chemical Abstract Services, STN Database Registry No. 138888-98-9, entered into STN Feb. 14, 1992.
Chemical Abstract Services, STN Database Registry No. 138240-34-3, entered into STN Jan. 10, 1992.
Chemical Abstract Services, STN Database Registry No. 60420-04-4, entered into STN Nov. 16, 1984.
Babic et al., "Heterocycles. CXLII Synthesis of some Triazoloazine 3-Oxides," *Journal of Heterocyclic Chemistry* 13:487-490 (1976).
Cmiljanovic et al., "PQR309: Structure-based design, synthesis and biological evaluation of novel, selective, dual pan-PI3K/mTOR inhibitor," Abstract, American Association for Cancer Research, Annual Meeting (2015).
Gomez-Garcia et al., "Tertiary formylated amines by microwave irradiation of N,N-dimethyl-N'-(2-pyridyl) formamidines with methyl vinyl ketone," *Heterocycl Commun* 20(1):21-23 (2014).

MANUFACTURING PROCESS FOR TRIAZINE, PYRIMIDINE AND PYRIDINE DERIVATIVES

FIELD OF THE INVENTION

The present invention relates to new manufacturing processes for triazine, pyrimidine and pyridine derivatives, to intermediates thereof and to the manufacturing of intermediates.

BACKGROUND OF THE INVENTION

WO 2010/052569 describes certain triazine, pyrimidine and pyridine derivatives having PI3K and mTOR inhibiting properties, their use as pharmaceuticals and manufacturing processes thereof. The manufacturing methods described are suitable to produce the described compounds reliably, but only in laboratory size.

One particular triazine compound disclosed in WO 2010/052569 is the dual phosphatidylinositol 3-kinase/mTOR inhibitor compound 5-(4,6-dimorpholino-1,3,5-triazin-2-yl)-4-(trifluoromethyl)pyridin-2-amine 1.

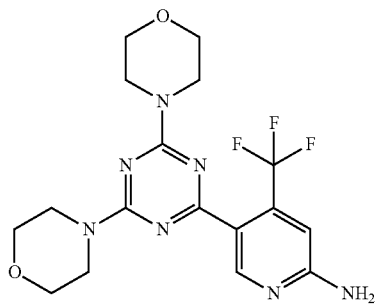

There remains a need for new solid forms for compound 1 suitable as active ingredients for medicaments, since this compound has hitherto only been available as an oil with low purity.

Biaryl structures such as compound 1 are often prepared using cross-coupling reactions. Among them, the Suzuki reaction is generally preferred due to the availability and the stability of organoboron reagents. However, organoboron reagents containing free amines present a particular challenge for cross-couplings since they are capable of poisoning the palladium-based catalyst and therefore diminishing the yield of desired product. In addition, the presence of a free amine generally leads to oily reagents that are not easy to isolate in pure form and above all difficult to handle in large scale syntheses.

SUMMARY OF THE INVENTION

The invention provides improved methods for manufacturing triazines, pyrimidines and pyridines of formula (I), new intermediates useful in such processes and methods for manufacturing such intermediates.

Thus, in one aspect, the invention relates to a method of manufacturing a compound of formula (I)

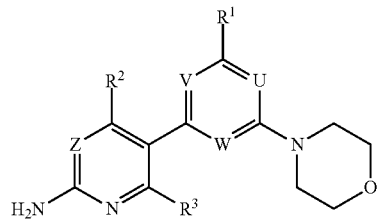

or a stereomer, tautomer or a salt thereof, wherein,

U is $CR^U$ or N, wherein $R^U$ is selected from the group consisting of hydrogen, cyano, halogen, methyl and trifluoromethyl;

V is $CR^V$ or N, wherein $R^V$ is selected from the group consisting of hydrogen, cyano, halogen, methyl and trifluoromethyl;

W is $CR^W$ or N, wherein $R^W$ is selected from the group consisting of hydrogen, cyano, halogen, methyl and trifluoromethyl;

provided that at least one of U, V and W is N;

Z is $CR^Z$ or N, wherein $R^Z$ is selected from the group consisting of hydrogen, cyano, halogen, methyl and trifluoromethyl;

$R^1$ is selected from the group consisting of hydrogen, halogen and $-N(R^T)R^S$, wherein $R^T$ and $R^S$ are hydrogen or $C_1$-$C_7$-alkyl, or wherein $R^T$ and $R^S$ together with the nitrogen to which they are attached form a $C_3$-$C_8$ mono- or bicyclic heterocyclic ring optionally containing one or more additional ring atoms selected from N, O or S, wherein said heterocyclic ring is optionally substituted with one or more groups independently selected from $C_1$-$C_7$-alkyl or $C_3$-$C_7$-cycloalkyl;

$R^2$ is selected from the group consisting of hydrogen, cyano, halogen, methyl and trifluoromethyl; and $R^3$ is hydrogen or halogen, characterized in that a compound of formula (II)

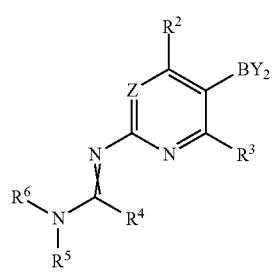

wherein $Y_2B$ represents a residue of an acyclic boronic acid, an acyclic boronic ester, or a cyclic boronic ester, and $R^2$ and $R^3$ are defined as for the compound of formula (I);

$R^4$ is hydrogen, $C_1$-$C_7$-alkyl or $C_5$-$C_7$-cycloalkyl;

$R^5$ and $R^6$ are $C_1$-$C_7$-alkyl, or $R^5$ and $R^6$ together represent $C_4$-$C_6$-cycloalkyl; and the crossed double bond between N and $C(R^4)N$ indicates a cis and/or trans double bond;

is reacted with a compound of formula (III)

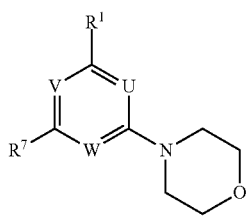

(III)

in which the groups U, V, W and $R^1$ are defined as above; and
$R^7$ is halogen;
in an aqueous organic solvent or an immiscible organic solvent-water mixture at temperatures from 0° C. to the boiling point of the solvent or solvent mixture in the presence of a Pd(0) or Pd(II) phosphine catalyst and a base; and the resulting formamidine of formula (IV)

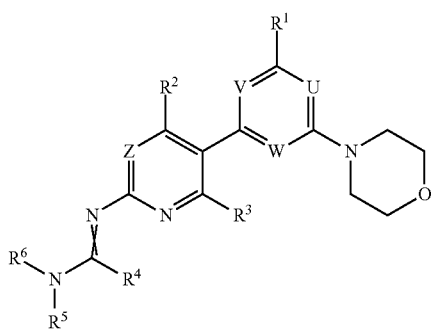

(IV)

wherein the substituents have the meanings as defined above,
is hydrolyzed, in situ or after isolation, in aqueous acid or basic solution.

In another aspect the invention relates to compounds of formula (II) as such, wherein the substituents have the meaning as mentioned above.

In yet another aspect the invention relates to a method of manufacturing a compound of formula (II), wherein the substituents have the meaning as mentioned above, characterized in that a compound of formula (V)

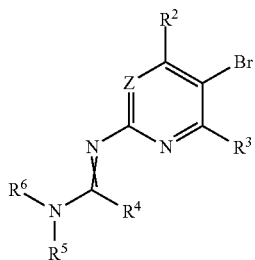

(V)

in which the groups $R^2$ to $R^6$ and the group Z are defined as above, is treated with an organometallic compound in an organic solvent at temperatures between −80° C. to the boiling point of the solvent and, after completion of the bromine-metal exchange reaction, is further reacted with an organoboron reagent of formula (VI)

$$R^8\text{—}BY_2 \qquad (VI)$$

wherein $R^8$ is a leaving group and Y is as defined above.

In another aspect the invention relates to compounds of formula (V) as such, wherein the substituents have the meaning as mentioned above.

In yet another aspect the invention relates to a method of manufacturing a compound of formula (V), wherein the substituents have the meaning as mentioned above, characterized in that a compound of formula (VII)

(VII)

in which the groups $R^2$, $R^3$ and Z are defined as above, is halogenated by bromine, copper(II)bromide, bromoxone or a N-haloimide, in an inert organic solvent, extracted with an aqueous base, and reacted with a compound of formula (VIII)

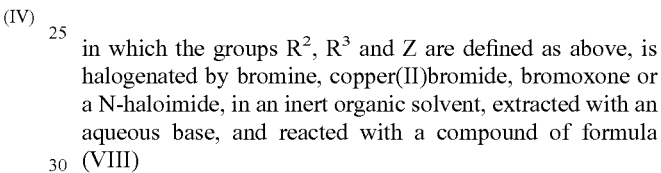

(VIII)

wherein $R^4$, $R^5$ and $R^6$ in formula (VIII) are defined as above, and $R^9$ is $C_1$-$C_4$-alkyl or $C_5$-$C_7$-cycloalkyl, preferably methyl, ethyl or t-butyl.

In another aspect, the invention relates to a method of manufacture of an acid addition salt of formula (Ia)

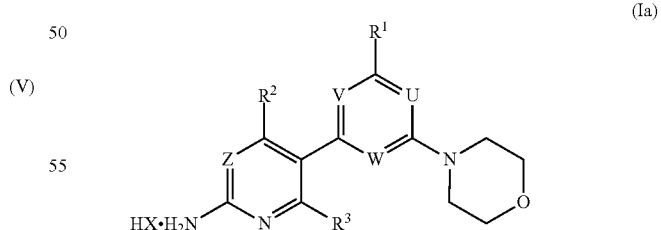

(Ia)

wherein
U, V, W, Z and $R^1$ to $R^3$ are as defined for a compound of formula (I), and HX is a protonic acid,
characterized in that a free base of formula (I) is treated with protonic acid HX, optionally in a suitable solvent, and the resulting add addition salt is purified by precipitation from a solvent or recrystallization.

Furthermore, the invention relates to the compound 5-(4,6-dimorpholino-1,3,5-triazin-2-yl)-4-(trifluoromethyl)pyridin-2-amine 1

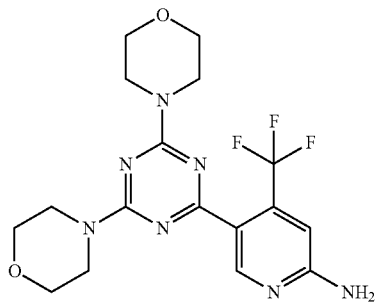

as a highly pure, preferably crystalline solid, its hydrates, salts and hydrates and solvates of its salts, and processes for the formation of such specific solid, preferably crystalline, forms.

DETAILED DESCRIPTION OF THE INVENTION

Figure 1:
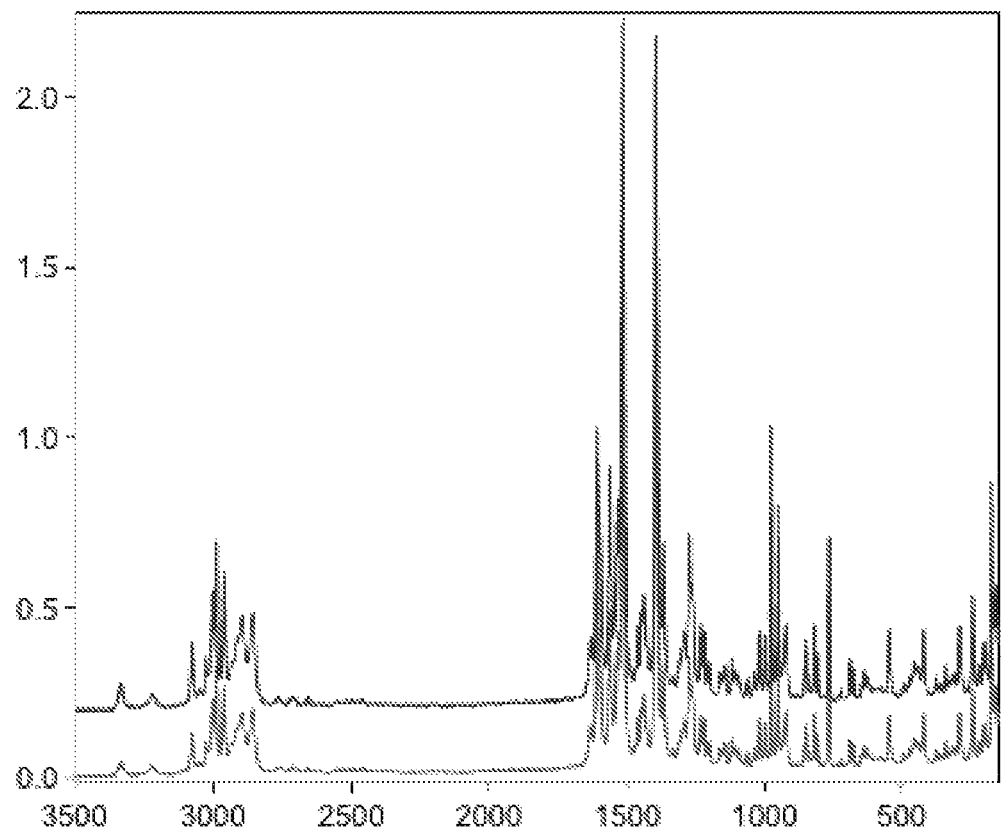
FIG. 1 depicts the FT-Raman spectra before and after dynamic vapor sorption (DVS) of 5-(4,6-dimorpholino-1,3,5-triazin-2-yl)-4-(trifluoromethyl)pyridin-2-amine 1.

The present invention provides a substantially improved method for the synthesis of compounds of formula (I)

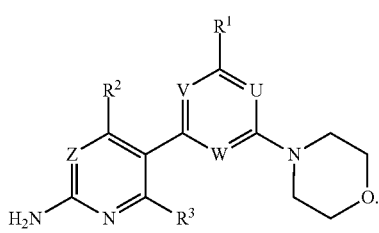

When compared to the methods disclosed in the prior art, e.g. in WO 2010/052569, the present method provides the compounds in higher yields and higher purity, and does not require hazardous chemicals. Furthermore, the described process is amenable to scale-up and simple to operate. For example, no extensive purification with chromatographic methods is required.

A central aspect of the present invention is the protection of a free amine function in the boron reagent to be used in the Suzuki reaction. The amidine group is a valuable alternative, delivering stable and readily available crystalline material that can be successfully employed in high-yield Suzuki reactions. The amidine protecting group can subsequently be removed by simple acidic or basic treatment to obtain the desired free amine adduct. This new strategy allows for the preparation of the desired compounds in higher yields and higher purity. Compound 1, for example, can be prepared on a kg-scale, with excellent yield and purity.

In particular the invention relates to a method of manufacture of a compound of formula (I), a stereomer, tautomer or a salt thereof, wherein U is $CR^U$ or N, wherein $R^U$ is selected from the group consisting of hydrogen, cyano, halogen, methyl and trifluoromethyl, preferably hydrogen;

V is $CR^V$ or N, wherein $R^V$ is selected from the group consisting of hydrogen, cyano, halogen, methyl and trifluoromethyl, preferably hydrogen;

W is $CR^W$ or N, wherein $R^W$ is selected from the group consisting of hydrogen, cyano, halogen, methyl and trifluoromethyl, preferably hydrogen;

provided that at least one of U, V and W is N;

Z is $CR^Z$ or N, wherein $R^Z$ is selected from the group consisting of hydrogen, cyano, halogen, methyl and trifluoromethyl, preferably hydrogen;

$R^1$ is selected from the group consisting of hydrogen, halogen, preferably chlorine, and $-N(R^T)R^S$, wherein $R^T$ and $R^S$ are, independently of each other, hydrogen or $C_1$-$C_7$-alkyl, preferably methyl or ethyl, or wherein $R^T$ and $R^S$ together with the nitrogen to which they are attached form a $C_3$-$C_8$ mono- or bicyclic heterocyclic ring optionally containing one or more additional ring atoms selected from N, O or S, wherein said heterocyclic ring is optionally substituted with one or more groups independently selected from $C_1$-$C_7$-alkyl or $C_3$-$C_7$-cycloalkyl, preferably methyl;

preferably wherein $R^T$ and $R^S$ together with the nitrogen to which they are attached form a $C_4$-$C_6$-heterocyclic ring containing one additional ring atom selected from O, N or S, such as in

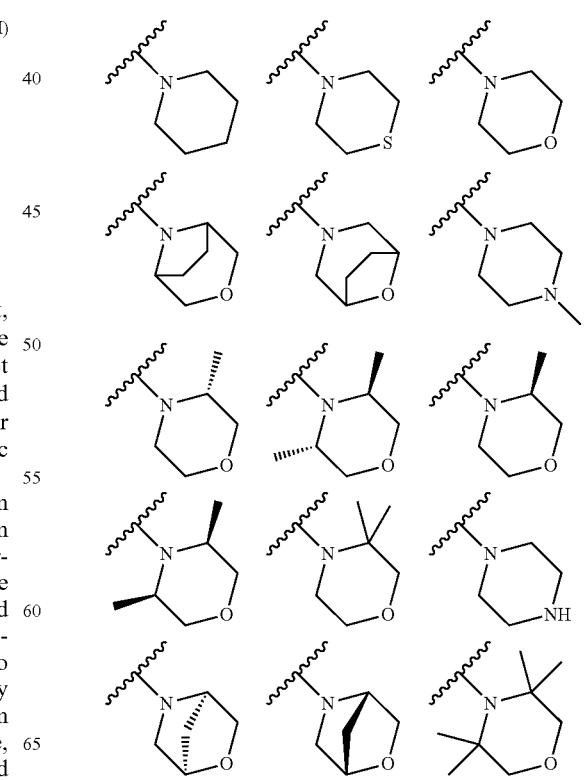

-continued

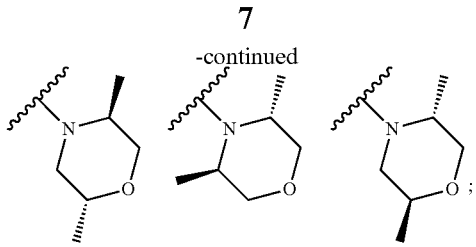

more preferably wherein $R^T$ and $R^S$ together with the nitrogen to which they are attached form morpholino;

$R^2$ is selected from the group consisting of hydrogen, cyano, halogen, methyl and trifluoromethyl, preferably hydrogen or trifluoromethyl and more preferably trifluoromethyl;

and $R^3$ is hydrogen or halogen, preferably hydrogen;

characterized in that a compound of formula (II)

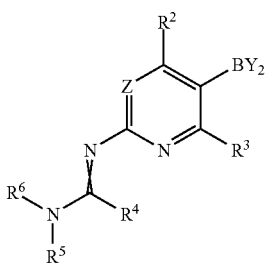

(II)

wherein $Y_2B$ represents a residue of a boronic acid; an acyclic boronic ester; or a cyclic boronic ester, preferably a cyclic boronic ester, in particular a pinacolato boronate, and $R^2$ and $R^3$ are defined as for the compound of formula (I);

$R^4$ is hydrogen, $C_1$-$C_7$-alkyl or $C_5$-$C_7$-cycloalkyl, preferably hydrogen or $C_1$-$C_7$-alkyl, in particular hydrogen;

$R^5$ and $R^6$ are $C_1$-$C_7$-alkyl, preferably $C_1$-$C_4$-alkyl, in particular methyl, or $R^5$ and $R^8$ together represent $C_4$-$C_6$-alkylene, in particular butylene;

and the crossed double bond between N and $C(R^4)N$ indicates a cis and/or trans double bond;

is reacted with a compound of formula (III)

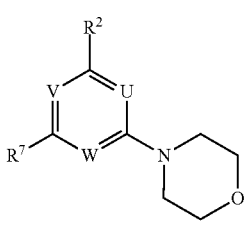

(III)

in which the groups U, V, W and $R^1$ are defined as above; and $R^7$ is halogen, preferably bromine or chlorine, in particular chlorine;

in an aqueous organic solvent or an immiscible organic solvent-water mixture at temperatures from 0° C. to the boiling point of the solvent or solvent mixture in the presence of a Pd(0) or Pd(II) phosphine catalyst and a base.

and the resulting formamidine of formula (IV)

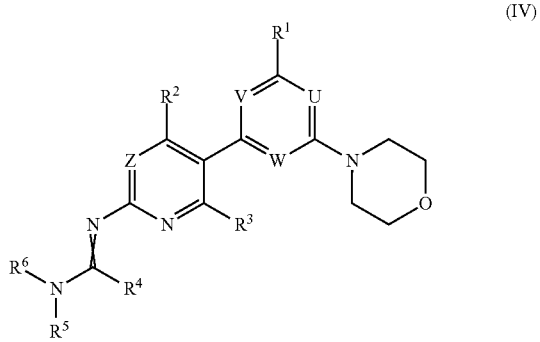

(IV)

wherein the substituents have the meanings as defined above, is hydrolyzed, in situ or after isolation, in aqueous acid or basic solution.

It has now been found that substantially improved yields can be achieved using formamidino protected organoboron reagents of formula (II), when compared to known method using free amines. Such amines give rise to side reactions, in particular aromatic nucleophilic substitution reactions involving said amine function and are thus leading to product mixtures reducing yields and necessitating chromatographic purification. Furthermore preparation of above-mentioned organoboron reagents with unprotected amine function, such as described in WO 2007/084786, is accompanied by the formation of difficult to separate proto-deborylated side products wherein the boron substituent is replaced by hydrogen. Preparation of N-acetyl protected organoboron reagents, such as described in WO 2012/044727, necessitates additional steps and requires cryogenic conditions (−78° C.). In comparison, organoboron reagents described herein can be prepared in pure form and good yield without extra steps and at temperatures not lower than 0° C. Furthermore, isolation of the herein described organoboron reagents in pure solid form, although easily achieved, is not a prerequisite for a successful Suzuki reaction. The herein described organoboron reagents can be used in situ thus saving further steps in the manufacturing of compounds of the formula (I).

Thus, in another embodiment of the method of manufacturing a compound of formula (I) of the present invention, said compound of formula (II) is generated in situ prior to said reaction with said compound of formula (III), wherein said generation in situ is effected by treating a compound of formula (V)

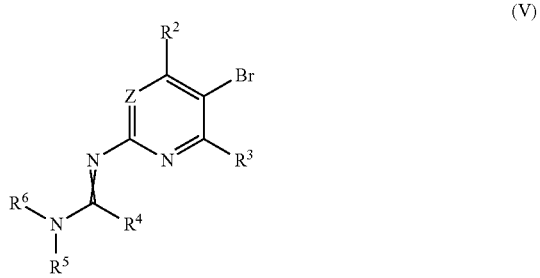

(V)

in which the groups $R^2$ to $R^6$ and the group Z are defined as indicated above, with an organometallic compound in an organic solvent at temperatures between −80° C. to the boiling point of the solvent and, after completion of the bromine-metal exchange reaction, is further reacted with an organoboron reagent of formula (VI)

$$R^8—BY_2 \qquad (VI)$$

wherein $R^8$ is a leaving group and Y is defined as indicated above.

This process and method, respectively, of manufacturing a compound of formula (I) of the present invention can optionally be followed by one or more salt forming reactions using protonic acid HX above and below and as described herein.

Alkyl is, for example, $C_1$-$C_7$-alkyl, such as $C_1$-$C_4$-alkyl, n-pentyl, 1-ethylpropyl, n-hexyl, 2-hexyl, isohexyl or n-heptyl, in particular $C_1$-$C_4$-alkyl, such as methyl, ethyl, n-propyl, isopropyl, n-butyl, sec-butyl, isobutyl or tert-butyl, in particular methyl or ethyl.

Halogen is fluoro, chloro, bromo or iodo, preferably fluoro or chloro, in particular chloro.

In a residue —$BY_2$ of an acyclic boronic ester, the ester substituents are, for example, $C_1$-$C_7$-alkoxy, such as methoxy, ethoxy, i-propoxy. In a residue —$BY_2$ of a preferred cyclic boronic ester, the dial forming the cyclic ester is preferably a 1,2-glycol, for example 1,2-ethanediol, 1,2-propanediol, 2,3-butanediol or, in particular, pinacol (2,3-dimethylbutane-2,3-diol). Further considered are also cyclic esters of a 1,3-glycol, for example 1,3-propanediol or 2,2-dimethyl-1,3-propanediol, also cyclic esters further containing nitrogen, such as cyclic esters of optionally substituted diethanolamine, e.g. N-phenyl-diethanolamine (N,N-di(2-hydroxyethyl)aniline), or of N-methylamine-diacetic acid. A leaving group $R^8$ is preferably a further group Y, e.g. $C_1$-$C_7$-alkoxy. In case of a cyclic boronate, wherein two Y groups represent a diol, the leaving group may likewise be $C_1$-$C_7$-alkoxy, in particular isopropoxy.

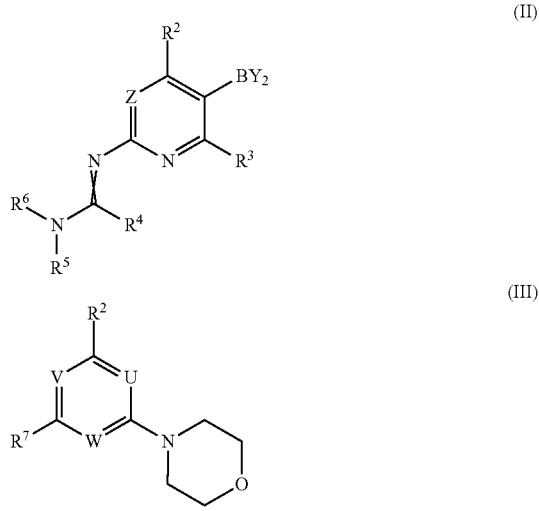

In a preferred embodiment of the present invention, wherein in said compound of formula (I), U is $CR^U$ or N, wherein $R^U$ is hydrogen; V is $CR^V$ or N, wherein $R^V$ is hydrogen; W is $CR^W$ or N, wherein $R^W$ is hydrogen; Z is $CR^Z$ or N, wherein $R^Z$ is hydrogen; $R^1$ is morpholino; $R^2$ is trifluoromethyl; and $R^3$ is hydrogen.

In a further preferred embodiment of the present invention, wherein in said compound of formula (II) $Y_2B$ represents a cyclic boronic ester; $R^4$ is hydrogen; and $R^5$ and $R^6$ are methyl.

Solvents to be used in the reaction of the organoboron reagent (II) with the compound of formula (III) are, for example, aqueous tetrahydrofuran, aqueous dioxane, or a toluene-water mixture. If the required base is added in aqueous solution, then the resulting solvent mixture is homogenous (tetrahydrofuran, dioxane) or heterogenous (toluene).

Palladium(0) and palladium(II) catalysts considered are tetrakistriphenyl-phosphine palladium(0), $Pd(dppf)Cl_2$, $Pd(dppf)Cl_2.CH_2Cl_2$, bis(triphenylphosphine)-palladium(II) dichloride, chloro(2-dicyclohexylphosphino-2',4',6'-triisopropyl-1,1'-biphenyl) [2-(2'-amino-1,1'-biphenyl)]-palladium(II), mixtures of a triarylphosphine, e.g. triphenylphosphine, tritolylphosphine or trifurylphosphine, or a dialkylarylphosphine, e.g. 2-dicyclohexyl-phosphino-2',4', 6'-triisopropyl-1,1'-biphenyl and a palladium salt, such as palladium acetate or palladium dichloride, in a ratio of 1-5:1, preferably in a ratio of 3-5:1, in particular 3:1. In a preferred embodiment, said Pd(0) or Pd(II) phosphine catalyst used in the inventive method of manufacturing said compound of formula (I) is a mixture of triphenyl-phosphine and palladium acetate in a ratio of 3:1.

The catalyst can be used in the presence of a base, e.g. potassium carbonate, potassium acetate, or tribasic potassium phosphate, preferably potassium carbonate, in particular potassium carbonate, preferably in the presence of an aqueous base, e.g. a solution of potassium carbonate in water, potassium acetate, or tribasic potassium phosphate, preferably solutions of potassium carbonate in water, in particular 10% (w/v) solutions of potassium carbonate in water.

The reaction is carried out in a solvent such as tetrahydrofuran, dioxane or toluene at a temperature comprised between 0° C. and the boiling point of the solvent for 1 to 48 h, preferably between 20° C. and the boiling point of the solvent for 1 to 24 h, more preferably between 40° C. and the boiling point of the solvent for 1 to 12 h, particularly preferred at the boning point of the solvent for 2 to 4 h.

In particular the reaction can be carried out in a mixture of tetrahydrofuran and water at a temperature between 0° C. and the boiling point of the solvent mixture for 1 to 48 h, preferably between 20° C. and the boiling point of the solvent mixture for 1 to 24 h, more preferably between 20 and 65° C. for 1 to 12 h, particularly preferred between 55 and 60° C. for 2 to 4 h, Alternatively the reaction can be carried out in a mixture of dioxane and water at a temperature between 0° C. and the boiling point of the solvent mixture for 1 to 48 h, preferably between 20° C. and the boiling point of the solvent mixture for 1 to 36 h, more preferably between 80 and 105° C. for 1 to 24 h, particularly preferred between 95 and 105° C. for 24 h.

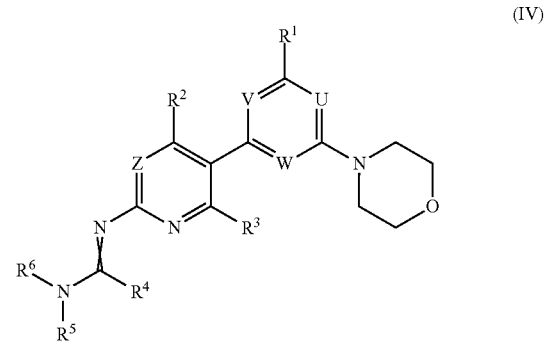

The compound of the formula (IV) obtained in such a reaction is then reacted in situ or after isolation with a suitable base, such as alkali hydroxide, preferably sodium hydroxide, or a suitable acid, such as hydrochloric acid, at concentrations of 1-10 M, preferably 2-8 M, in particular 4-5 M to obtain, after neutralization, a compound of the formula (I).

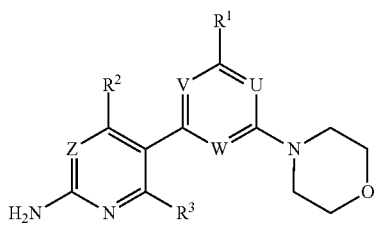

(I)

In another embodiment of the method of manufacturing a compound of formula (I) of the present invention, in said compound of formula (I), formula (II), formula (III) and formula (IV), where applicable, U is $CR^U$ or N, wherein $R^U$ is hydrogen; V is $CR^V$ or N, wherein $R^V$ is hydrogen; W is $CR^W$ or N, wherein $R^W$ is hydrogen; Z is $CR^Z$ or N, wherein $R^Z$ is hydrogen; $R^1$ is halogen, preferably chlorine; $R^2$ is trifluoromethyl; and $R^3$ is hydrogen; and wherein further said resulting formamidine of formula (IV) is reacted with morpholine prior to said its hydrolyzation, wherein preferably said formamidine of formula (IV) is isolated for said reaction with said morpholine. Further preferably, in said compound of formula (II) $Y_2B$ represents a cyclic boronic ester; $R^4$ is hydrogen; and $R^5$ and $R^6$ are methyl.

In a preferred embodiment of the method of manufacturing a compound of formula (I) of the present invention, in said compound of formula (I), formula (II), formula (III) and formula (IV), where applicable, U is N; V is N; W is N; Z is $CR^Z$, wherein $R^Z$ is hydrogen; $R^1$ is halogen, preferably chlorine, or morpholino; $R^2$ is trifluoromethyl; and $R^3$ is hydrogen.

In a further very preferred embodiment of the method of manufacturing a compound of formula (I) of the present invention, in said compound of formula (I), formula (II), formula (III) and formula (IV), where applicable, U is N; V is N; W is N; Z is $CR^Z$, wherein $R^Z$ is hydrogen; $R^1$ is morpholino; $R^2$ is trifluoromethyl; and $R^3$ is hydrogen.

In a further very preferred embodiment of the method of manufacturing a compound of formula (I) of the present invention, in said compound of formula (I), formula (II), formula (III) and formula (IV), where applicable, U is N; V is N; W is N; Z is $CR^Z$, wherein $R^Z$ is hydrogen; $R^1$ is morpholino; $R^2$ is trifluoromethyl; and $R^3$ is hydrogen, and wherein in said compound of formula (II) $Y_2B$ represents a cyclic boronic ester; $R^4$ is hydrogen; and preferably $R^5$ and $R^6$ are methyl. Preferably said $R^7$ is chlorine.

In again a further very preferred embodiment of the method of manufacturing a compound of formula (I) of the present invention, in said compound of formula (I), formula (II), formula (III) and formula (IV), where applicable, U is N; V is N; W is N; Z is $CR^Z$, wherein $R^Z$ is hydrogen; $R^1$ is morpholino; $R^2$ is trifluoromethyl; and $R^3$ is hydrogen, and wherein in said compound of formula (II) $Y_2B$ represents a cyclic boronic ester, and preferably a pinacolato boronate; $R^4$ is hydrogen; and $R^5$ and $R^6$ are methyl. Preferably said $R^7$ is chlorine.

In again a further very preferred embodiment of the method of manufacturing a compound of formula (I) of the present invention, in said compound of formula (I), formula (II), formula (III) and formula (IV), where applicable, U is N; V is N; W is N; Z is $CR^Z$, wherein $R^Z$ is hydrogen; $R^1$ is morpholino; $R^2$ is trifluoromethyl; and $R^3$ is hydrogen, and wherein in said compound of formula (II) $Y_2B$ represents a pinacolato boronate; $R^4$ is hydrogen; and $R^5$ and $R^6$ are methyl. Preferably said $R^7$ is chlorine.

In another aspect, the invention relates to a method of manufacture of an acid addition salt of formula (Ia)

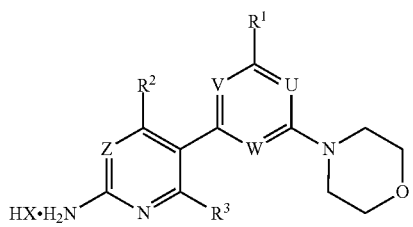

(Ia)

wherein

U, V, W, Z and $R^1$ to $R^3$ are as defined for a compound of formula (I), and HX is a protonic add, characterized in that a free base of formula (I) is treated with protonic acid HX, optionally in a suitable solvent, and the resulting acid addition salt is purified by precipitation from a solvent or recrystallization.

The conversion of free compounds into their corresponding salts is well known in organic chemistry. Basic compounds, as in the present invention, may be converted to the respective salts by addition of acidic compounds (HX), e.g., dissolved in organic or aqueous medium, as gas or in substance. This reaction was not yet applied using the particular starting materials as described herein and thus forms a new and inventive process.

This step is preferably used to produce pharmaceutically acceptable acid addition salts from a compound of formula (I). Preferred pharmaceutically acceptable acid addition salts are formed from the following protonic acids HX: i) inorganic acids, in particular selected from the group consisting of hydrochloric acid, hydroboric acid, nitric acid, sulfuric acid and phosphoric acid, ii) organic acids, in particular selected from the group consisting of formic acid, acetic acid, trifluoroacetic acid, fumaric acid, tartaric acid, oxalic acid, maleic acid, citric acid, methanesulfonic acid, succinic acid, malic acid, benzenesulfonic acid and p-toluenesulfonic acid, and iii) acidic amino acids, in particular selected from the group consisting of aspartic acid and glutamic acid. A particularly preferred acid HX is hydrochloric acid. A further preferred acid HX is methanesulfonic acid.

In another aspect the invention relates to compounds of formula (II) as such,

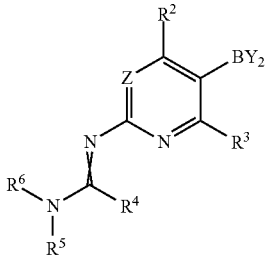

(II)

wherein
$Y_2B$ represents a residue of a boronic acid, an acyclic boronic ester, or a cyclic boronic ester, preferably a cyclic boronic ester, in particular a pinacolato boronate;
$R^2$ is hydrogen, cyano, halogen, methyl or trifluoromethyl, preferably hydrogen or trifluoromethyl, in particular trifluoromethyl;
$R^3$ is hydrogen or halogen, preferably hydrogen;
$R^4$ is hydrogen, $C_1$-$C_7$-alkyl or $C_5$-$C_7$-cycloalkyl, preferably hydrogen or $C_1$-$C_7$-alkyl, in particular hydrogen;
$R^5$ and $R^6$ are $C_1$-$C_7$-alkyl, preferably $C_1$-$C_4$-alkyl, in particular methyl, or $R^5$ and $R^6$ together represent $C_4$-$C_6$-alkylene, in particular butylene;
and the crossed double bond between N and $C(R^4)N$ indicates a cis and/or trans double bond.

In a very preferred embodiment of the present inventive compound of formula (II), said Z is $CR^Z$, wherein $R^Z$ is hydrogen; $R^3$ is hydrogen, $Y_2B$ represents a cyclic boronic ester, and preferably a pinacolato boronate; $R^4$ is hydrogen; and $R^5$ and $R^6$ are methyl.

In a very preferred embodiment of the present inventive compound of formula (II), said Z is $CR^Z$, wherein $R^Z$ is hydrogen; $R^3$ is hydrogen, $Y_2B$ is a pinacolato boronate; $R^4$ is hydrogen; and $R^5$ and $R^6$ are methyl.

In yet another aspect the invention relates to a method of manufacturing a compound of formula (II), wherein the substituents have the meaning as mentioned above, characterized in that a compound of formula (V)

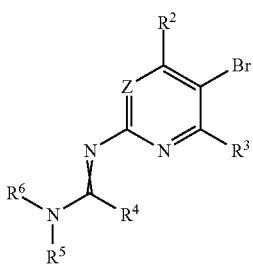

(V)

in which the groups $R^2$ to $R^6$ and the group Z are defined as above, is treated with an organometallic compound in an organic solvent at temperatures between −80° C. to the boiling point of the solvent and, after completion of the bromine-metal exchange reaction, is further reacted with an organoborate (VI)

 (VI)

wherein $R^8$ is a leaving group and Y is as defined above.

In a very preferred embodiment of the method of manufacturing a compound of formula (II) of the present invention, in said compound of formula (II), (V) and (VI), where applicable, said Z is $CR^Z$, wherein $R^Z$ is hydrogen; $R^3$ is hydrogen, $Y_2B$ represents a cyclic boronic ester, and preferably a pinacolato boronate; $R^4$ is hydrogen; and $R^5$ and $R^6$ are methyl.

In a further very preferred embodiment of the method of manufacturing a compound of formula (II) of the present invention, in said compound of formula (II), (V) and (VI), where applicable, said Z is $CR^Z$, wherein $R^Z$ is hydrogen; $R^3$ is hydrogen, $Y_2B$ represents a cyclic boronic ester, and preferably a pinacolato boronate; $R^4$ is hydrogen; and $R^5$ and $R^6$ are methyl, In the manufacture of a compound of the formula (II), a compound of the formula (V)

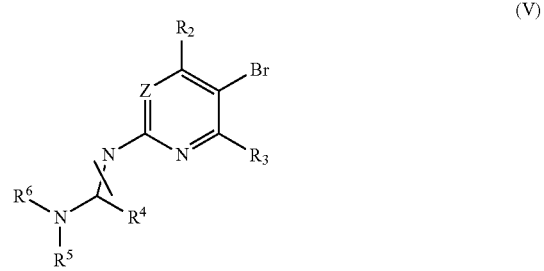

(V)

is subjected to bromine-metal exchange by methods known in the art, such as, reaction with organometallic compounds, preferably organolithium and organomagnesium compounds, in particular isopropylmagnesium chloride, in a suitable solvent such as tetrahydrofuran or 2-methyl-tetrahydrofuran at temperatures between −80° C. and the boiling point of the solvent, preferably between −20° C. and the boiling point of the solvent, in particular between 0° C. and 65° C. After completion of the bromine-metal exchange the formed organometallic compound is reacted in situ with the corresponding boron reagent $R^8$—$BY_2$ of formula (VI), wherein Y is as defined above and leaving group $R^8$ is selected from halogen or $C_1$-$C_4$ alkoxy, preferably from methoxy or isopropoxy, most preferably isopropoxy, in particular with 2-isopropoxy-4,4,5,5-tetramethyl-1,3,2-dioxaborolane, to obtain the preferred compound of the formula (II). The compound of the formula (II) can be further used in situ or isolated in pure form.

In another aspect the invention relates to compounds of formula (V)

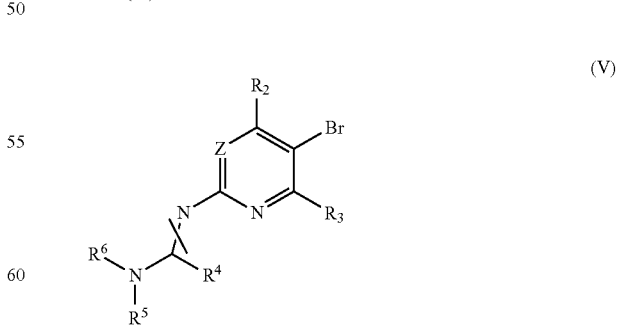

(V)

as such, wherein
Z is $CR^Z$ or N, wherein $R^Z$ is selected from the group consisting of hydrogen, cyano, halogen, methyl and trifluoromethyl;

$R^2$ is hydrogen, cyano, halogen, methyl or trifluoromethyl, preferably hydrogen or trifluoromethyl, in particular trifluoromethyl;

$R^3$ is hydrogen or halogen, preferably hydrogen;

$R^4$ is hydrogen, $C_1$-$C_7$-alkyl or $C_5$-$C_7$-cycloalkyl, preferably hydrogen or $C_1$-$C_7$-alkyl, in particular hydrogen;

$R^5$ and $R^6$ are $C_1$-$C_7$-alkyl, preferably $C_1$-$C_4$-alkyl, in particular methyl; or $R^5$ and $R^6$ together represent $C_4$-$C_6$-alkylene, in particular butylene;

and the crossed double bond between N and $C(R^4)N$ indicates a cis and/or trans double bond.

In a very preferred embodiment of the present inventive compound of formula (V), said Z is $CR^Z$, wherein $R^Z$ is hydrogen; $R^2$ is trifluoromethyl; $R^3$ is hydrogen; $R^4$ is hydrogen; and $R^5$ and $R^6$ are methyl.

In yet another aspect the invention relates to a method of manufacturing a compound of formula (V). Compounds of formula (V) are obtained from a compound of the formula (VII)

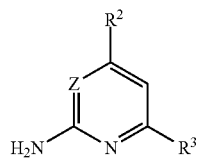

(VII)

in which the groups $R^2$, $R^3$ and Z are defined as above.

The compounds of the formula (VII) are halogenated with halogenating agents, such as bromine, copper(II)bromide, bromoxone or N-haloimides, preferably N-halosuccinimides, in particular N-bromosuccinimide, in an inert organic solvent, such as an ester, ether or nitrile solvent, preferably $C_1$-$C_4$-alkyl acetic acid esters, $C_1$-$C_4$-alkyl nitriles or cyclic ethers, in particular acetic acid ethyl ester, acetonitrile, or 2-methyltetrahydrofuran. Then the reaction mixture is extracted with a suitable aqueous base, such as metal carbonate, preferably alkali metal carbonate, in particular sodium and potassium carbonate solutions in water. The obtained halogenated intermediate is further reacted, either in situ or after isolation of the intermediate, with a compound of the formula (VIII)

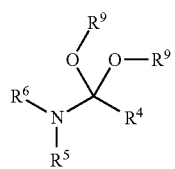

(VIII)

wherein $R^4$, $R^5$ and $R^6$ in formula (VIII) are defined as above, and $R^9$ is $C_1$-$C_4$-alkyl or $C_5$-$C_7$-cycloalkyl, preferably $C_1$-$C_4$-alkyl, in particular methyl, ethyl or t-butyl.

In a very preferred embodiment of the method of manufacturing a compound of formula (V) of the present invention, in said compound of formula (VII) and (VIII), where applicable, said Z is $CR^Z$, wherein $R^Z$ is hydrogen; $R^2$ is trifluoromethyl; $R^3$ is hydrogen; $R^4$ is hydrogen; and $R^5$ and $R^6$ are methyl.

Compounds of Formula (III)

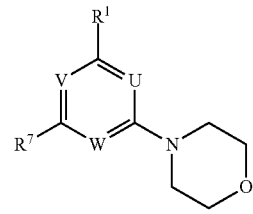

(III)

in which the groups U, V, W and $R^1$ are defined as above, $R^7$ is halogen, preferably bromine or chlorine, in particular chlorine, are obtained from compounds of formula (IX), in which U, V, W and $R^7$ are defined as above, by methods for aromatic nucleophilic substitution known in the art.

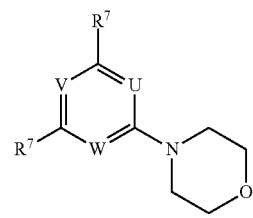

(IX)

Compounds of the formula (IX) are obtained from corresponding compounds of formula (X)

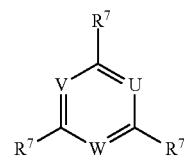

(X)

wherein $R^7$ is halogen, by reaction with morpholine in suitable organic solvents, such as alkanes, haloalkanes, esters, ethers, nitriles, preferably haloalkanes, in particular dichloromethane. In the particular situation wherein $R^1$ in compound of formula (III) is morpholine, this compound is directly obtained from a compound of the formula (X) by reaction with excess morpholine in the mentioned suitable organic solvents, e.g. dichloromethane.

Furthermore, the invention relates to the compound 5-(4,6-dimorpholino-1,3,5-triazin-2-yl)-4-(trifluoromethyl)pyridin-2-amine 1

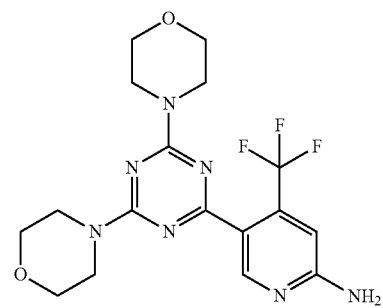

1 in solid, highly pure form, preferably of more than 99°/h purity, more preferably of more than 99.5% purity, for example 99.7% purity, melting at 219-220° C.

In still other aspects, the invention relates to specific highly pure solid, preferably crystalline, forms of the compound of formula 1, its hydrates, its salts and hydrates and solvates of its salts, and processes for the formation of such specific solid, preferably crystalline, forms.

EXAMPLES eq=equivalents
TLC=thin layer chromatography

Example 1a: Preparation of 4-(4-chloro-6-morpholino-1,3,5-triazin-2-yl)morpholine

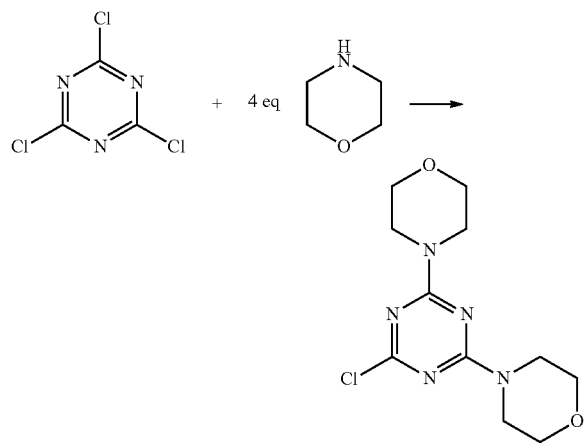

A mixture of morpholine (2.83 kg, 2.84 L, 32.5 mol, 4 eq), water (6.75 L) and dichloromethane (5 L) was cooled to 5° C. To the resulting biphasic mixture was added a solution of cyanuric chloride (1.50 kg, 8.13 mol, 1 eq) in dichloromethane (4.5 L) at such a rate that the temperature did not exceed 10° C. (ca. 3 h), and stirring was continued for 15 min at 5° C. The phases were separated and the organic phase was washed twice with water (2×15 L). The volume of the organic phase was reduced to half by evaporation under reduced pressure (700 mbar) using a rotary evaporator. Solvent switch was performed by gradual addition of heptane isomers (15 L) and evaporation of a total of 14.5 L of solvent under reduced pressure (150 mbar) using a rotary evaporator. The resulting white suspension was cooled down to 20° C. and stirred at this temperature for 18 h. The product was collected by filtration, washed with heptane isomers (1.4 L) and dried at 35° C. under reduced pressure (<50 mbar) to constant weight to yield the title compound as a white solid (2.297 kg, 7.97 mol, 98% yield).

$^1$H NMR (400 MHz, CDCl$_3$, δ): 3.78 (m, 8H), 3.70 (m, 8H).

MS m/z: 287.6 [M+H]$^+$.

TABLE 1

| Comparative yields | | |
|---|---|---|
| | This invention | WO2010052569 |
| Scale | 2.3 kg | 890 mg |
| Yield | 98% | 56% |

Example 1b: Preparation of 4-(4-chloro-6-morpholino-1,3,5-triazin-2-yl)morpholine The preparation described in Example 1b was effected in a modified manner as compared to the procedure described in Example 1a leading to a further improved purity.

To a solution of morpholine (9.21 kg, 9.20 L, 106 mol, 4 eq) in water (21.9 L) was added dichloromethane (14.6 L) and the mixture was cooled to 0° C. To the resulting biphasic mixture was added a solution of cyanuric chloride (4.87 kg, 26.4 mol, 1 eq) in dichloromethane (34.1 L) at a constant rate during 3 h (so that the temperature did not exceed 5° C.) and stirring was continued for 15 min at 5° C. The phases were separated and the organic phase was washed three times with water (3×29.2 L) and dried over anhydrous sodium sulfate (3 kg). The solids were removed by filtration and the filter cake was washed with dichloromethane (9.7 L). To the combined filtrates was added heptane (39 L) and the volume (102 L) was reduced by 68 L by evaporation under reduced pressure (ca 700 mbar). To the resulting mixture was added heptane (14.6 L) and the resulting white suspension was cooled to 3° C. during 1.5 h. The product was collected by filtration, washed with heptane (2×14.6 L) and dried at 40° C. under reduced pressure (<50 mbar) to constant weight to yield the title compound as white solid (7.35 kg, 25.72 mol, 97% uncorrected yield, purity 97% a/a). In a second run starting from 4.40 kg cyanuric chloride the title compound was obtained as white solid by the same procedure (6.57 kg, 22.99 mol, 94% uncorrected yield, purity 97% a/a). The two batches of the title compound were slurried together in heptane (110 L) and stirred at 21° C. for 18 h. The solid was collected by filtration and the filter cake was washed with heptane (10 L) and dried to constant weight at 40° C. under vacuum to yield 13.6 kg (98% recovery, purity 98.3% a/a). This material was divided into two equal batches for recrystallization. To a stirred solution of the above obtained title compound (6.8 kg) in dichloromethane (20 L) at 40° C. was added heptane (60 L) during 1.5 h at 40° C. and stirring was continued for 0.75 h. The resulting suspension was cooled to 0° C. during 8 h. The solid was collected by filtration washed with a mixture of heptane and dichloromethane (99:1, 7 L) and dried to constant weight under vacuum at 40° C. to yield 6.13 kg and 6.03 kg. Both batches were combined to yield 12.16 kg (84% overall, purity 99.9% a/a) of the title compound.

Example 2a: Preparation of N'-[5-bromo-4-(trifluoromethyl)-2-pyridyl]-N,N-dimethyl-formamidine

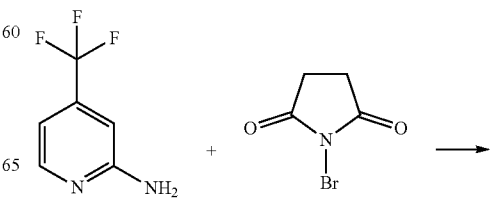

19

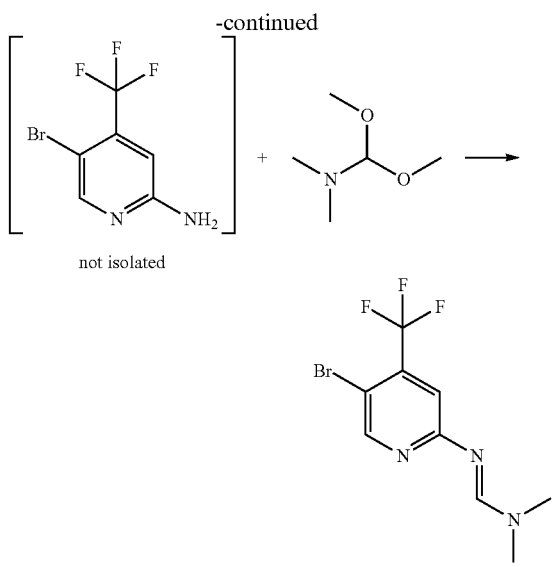

not isolated

To a solution of 4-(trifluoromethyl)pyridin-2-amine (1.39 kg, 8.59 mol, 1 eq) in 2-methyl-tetrahydrofuran (16.8 L) was added N-bromosuccinimide (1.528 kg, 8.59 mol, 1 eq) in 10 equal portions during 50 min at a temperature of 0° C., and stirring was continued at this temperature for additional 2 h. To the resulting orange slurry was added an 8% aqueous solution of sodium carbonate (14 L). The phases were separated and the aqueous phase was extracted with 2-methyltetrahydrofuran (2.4 L). The combined organic phases were mixed with a 5% aqueous solution of sodium chloride (5.6 L) and the phases were separated. The organic phase was azeotropically distilled with 2-methyltetrahydrofuran (2×9 L) and the volume of the brown solution was reduced to 18 L by evaporation under reduced pressure using a rotary evaporator. To the resulting solution was added at 35° C. 1,1-dimethoxy-N,N'-dimethylmethanamine (1.275 kg, 1.52 L, 10.7 mol, 1.25 eq and the mixture was heated to 60° C. for 2.5 h. The mixture was cooled to room temperature and the solvent was switched to heptane isomers by azeotropic distillation (4 times) under reduced pressure using heptane isomers (4×9 L). Heptane isomers were added to reach a volume of 28 L. A dark brown precipitate was removed by filtration, the resulting brown mother liquor was washed twice with water (2×14 L). The volume of the organic phase was reduced to 7 L by evaporation under reduced pressure whereby a suspension formed. This suspension was stirred at 20° C. for 1 h and then cooled down to 0° C. The solid was collected by filtration, washed with cold heptane isomers (2 L) and dried to constant weight under reduced pressure (<50 mbar) to yield the title compound as an orange solid (1.85 kg, 6.20 mol, 73% yield).

$^1$H NMR (400 MHz, CDCl$_3$, δ): 8.47 (s, 1H, pyridyl-H), 8.40 (s, 1H, pyridyl-H), 7.20 (s, 1H, CH(N(Me)$_2$), 3.12 (s, 3H, CH$_3$), 3.10 (s, 3H, CH$_3$);

$^{19}$F NMR (100.6 MHz, CDCl$_3$, δ): −65.01.

MS m/z: 296.0 [M($^{79}$Br)+H]$^+$, 298.0 [M($^{81}$Br)+H]$^+$.

Example 2b: Preparation of N'-[5-bromo-4-(trifluoromethyl)-2-pyridyl]-N,N-dimethyl-formamidine The preparation described in Example 2b was effected in a modified manner as compared to the procedure described in Example 2a leading to a further improved purity.

20

To a solution of 4-(trifluoromethyl)pyridine-2-amine (6.50 kg, 40.1 mol, 1 Eq) in 2-methyltetrahydrofuran (78 L) was added at 0° C. in ten equal portions N-bromosuccinimide (7.49 kg, 42.1 mol, 1.05 Eq) during 50 min. The resulting suspension was stirred at 0° C. for 1 h. The solids were removed by filtration. The filter cake was washed with 2-methyl-tetrahydrofuran (10 L). The combined filtrates were mixed with 4% aqueous sodium carbonate (65 L). The phases were separated and the organic phase was extracted with 2N hydrochloric acid (3×20 L and 3×10 L). The combined aqueous extracts were mixed with 2-methyl-tetrahydrofuran (5 L), deionized water (3 L) and an aqueous sodium hydroxide solution (30% w/v, 19 L) at such a rate that the temperature did not exceed 20° C. The pH of the resulting biphasic mixture was adjusted to 8 by addition of a saturated aqueous sodium bicarbonate solution (8% w/v, 3.4 L). The phases were separated and the slightly turbid brown organic phase was dried over anhydrous sodium sulfate (3.2 kg). The solids were removed by filtration and the filter cake was washed with 2-methyl-tetrahydrofuran (5 L). The solvent was evaporated under reduced pressure. The resulting brown oil (8.35 kg) was dissolved in 2-methyltetrahydrofuran (94 L) at 60° C. and 1,1-dimethoxy-N,N'-dimethylmethanamine (6.8 L, 51.2 mol, 1.28 Eq) was added during 10 min. The resulting brown solution was stirred at 60° C. for 3 h cooled to 20° C. and mixed with a saturated aqueous sodium bicarbonate solution (8% w/v, 33 L). The phases were separated and the organic phase was washed twice with an aqueous sodium chloride solution (5% w/v, 32 L). The organic phase was dried over anhydrous sodium sulfate (3.2 kg). The solids were removed by filtration and the filtercake was washed with 2-methyl-tetrahydrofuran (11 L). The combined filtrates were mixed with heptane (39 L) and the mixture was concentrated under reduced pressure. The residue was mixed with heptane (39 L) and the mixture was concentrated under reduced pressure whereby a suspension formed. The suspension was stirred at 0° C. The solid was collected by filtration and washed with heptane (8 L) to yield the title compound (8.20 kg, 27.7 mol, 69%, purity 98.0% a/a) as yellow-brownish solid.

Example 3a: Preparation of (E)-N,N-dimethyl-N'-(5-(4,4,5,5-tetramethyl-1,3,2-dioxaborolan-2-yl)-4-(trifluoromethyl)pyridin-2-yl)formamidine

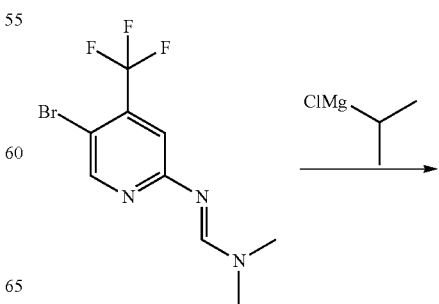

-continued

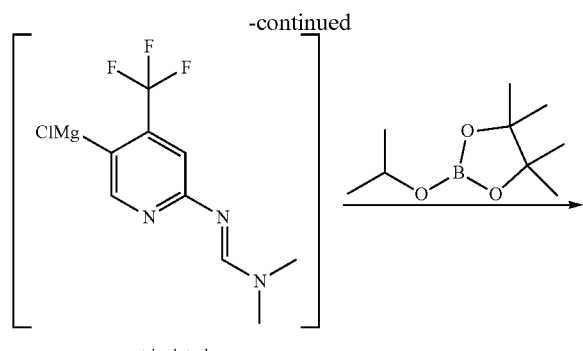

not isolated

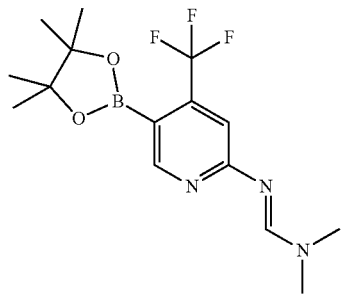

To a 2 M solution of isopropylmagnesium chloride (29.3 mL, 1.15 eq) in THF (60 mL) was slowly added at 0° C. a solution of N'-[5-bromo-4-(trifluoromethyl)-2-pyridyl]-N,N-dimethyl-formamidine (Example 2, 15.06 g, 50.9 mmol, 1 eq) in THF (50 mL) during 5 min. The mixture was stirred at 0° C. for 45 min and at room temperature for 15 min. TLC monitoring confirmed full bromine-magnesium exchange. To the resulting suspension 2-isopropoxy-4,4,5,5-tetramethyl-1,3,2-dioxaborolane (13.4 mL, 1.3 eq) was added and the mixture was stirred at 60° C. for 3 h. the resulting dark solution was cooled to 0° C. and quenched by addition of 15% aqueous solution of NH$_4$Cl (210 mL). The layers were separated, and the aqueous layer was further extracted with THF (100 mL). The combined organic layers were dried over anhydrous sodium sulfate, filtered, and the solvent was removed under reduced pressure using a rotary evaporator. Heptane (200 mL) was added and the resulting solution was washed with a saturated aqueous solution of NaHCO$_3$ (100 mL). The organic layer was dried over anhydrous Na$_2$SO$_4$, filtered, and the solvent volume was reduced to 100 mL using a rotary evaporator. The resulting orange solution was cooled to −20° C. for 18 h. Yellow-orange crystals of the title compound (11.45 g, 66% yield) were collected by filtration. The mother liquor was concentrated and subjected to a second recrystallization from heptane to afford further yellow-orange crystals of the title compound (1.18 g, 7% yield). Combined yield of the reaction was 73%.

$^1$H NMR (CDCl$_3$, 400 MHz, δ): 8.70 (s, 1H), 8.61 (s, 1H), 7.17 (s, 1H), 3.13 (s, 3H), 3.11 (s, 3H), 1.35 (s, 12H).
$^{19}$F NMR (CDCl$_3$, 376 MHz, δ): −62.7 (s, 3F).
MS m/z: 344.8 [M+H]+.

Example 3b: Preparation of (E)-N,N-dimethyl-N'-(5-(4,4,5,5-tetramethyl-1,3,2-dioxaborolan-2-yl)-4-(trifluoromethyl)pyridin-2-yl)formamidine The preparation described in Example 3b was effected in a modified manner as compared to the procedure described in Example 3a leading to a further improved purity.

A 2M solution of isopropylmagnesiumchloride in tetrahydrofuran (17.46 kg, 33.8 mol, 1.25 Eq) was added to tetrahydrofuran (32 L) at 0° C. during 50 min. To the resulting solution was added a solution of N'-[5-bromo-4-(trifluoromethyl)-2-pyridyl]-N,N-dimethyl-formamidine (8.0 kg, 27 mol, 1 Eq) in tetrahydrofuran (28 L) during 30 min at 0 to −4° C. The resulting orange suspension was stirred at 0° C. for 16 min and then warmed to 20° C. during 35 min at which temperature stirring was continued for 18 min. To the resulting orange suspension was added 2-isopropoxy-4,4,5,5-tetramethyl-1,3,2-dioxaborolane (6.84 kg, 7.48 L, 36.7 mol, 1.36 Eq) during 8 min. The resulting mixture was heated to 55° C. during 50 min and kept stirring at this temperature for 4.5 h. The resulting solution was cooled to 0° C. and an ice cold 15% aqueous solution of ammonium chloride (64 L) was added during 17 min keeping the temperature between 1 to 8° C. The biphasic mixture was stirred for 36 min, the phases were separated and the organic phase was washed 3× with an aqueous sodium chloride solution (13% w/v, 3×40 L). The solvent was evaporated under reduced pressure at 40° C. The resulting residue was dissolved in heptane (102 L), washed with saturated aqueous sodium bicarbonate solution (8% w/v, 55 L) and dried over anhydrous sodium sulfate (3.2 kg). The solids were removed by filtration and the filter cake was washed with heptane (11 L). The combined filtrates were concentrated to a volume of ca 32 L whereby a yellow brownish suspension formed. This suspension was cooled to −20° C. and stirred at this temperature for 3 h. The solid was collected by filtration and washed twice with cold heptane (2×6 L) and dried to constant weight under reduced pressure at 40° C. to yield the title compound (6.01 kg, 17.5 mol, 65%, purity 99% a/a).

Example 4a: Preparation of 5-(4,6-dimorpholino-1,3,5-triazin-2-yl)-4-(trifluoromethyl)pyridin-2-amine

1

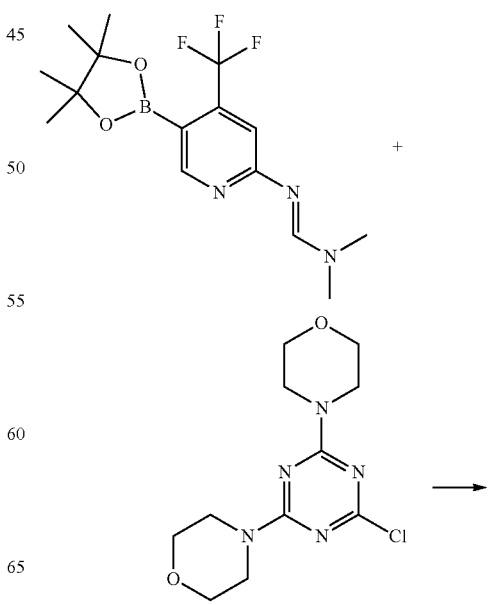

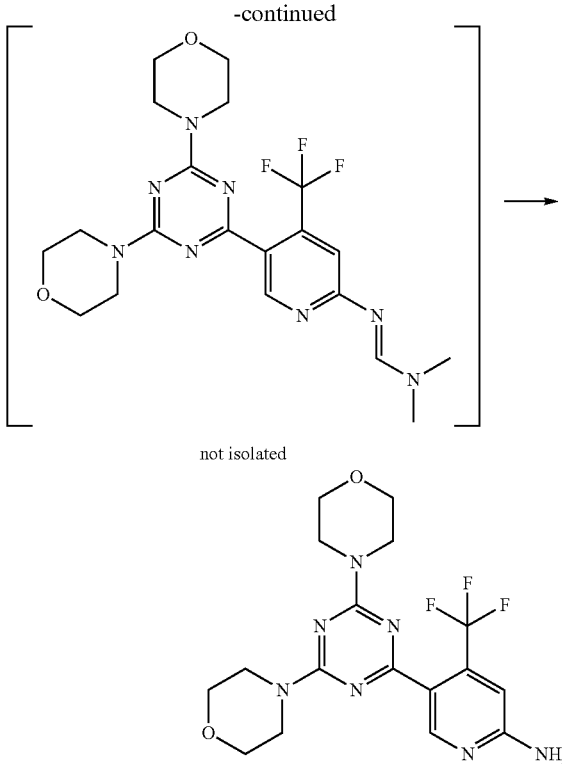

not isolated

A mixture of palladium acetate (18 mg, 0.08 mmol, 0.04 eq) and triphenylphosphine (63 mg, 0.24 mmol, 0.12 eq) in tetrahydrofuran (6.25 mL) was stirred at room temperature for 1 h. To the resulting solution was added a solution of 4-(4-chloro-6-morpholino-1,3,5-triazin-2-yl)morpholine (Example 1, 572 mg, 2 mmol, 1 eq) and (E)-N,N-dimethyl-N'-(5-(4,4,5,5-tetramethyl-1,3,2-dioxaborolan-2-yl)-4-(trifluoromethyl)pyridin-2-yl)formamidine (Example 3, 823 mg, 2.4 mmol, 1.2 eq) in tetrahydrofuran (5 mL) and a solution of potassium carbonate (828 mg, 6 mmol, 3 eq) in water (2.5 mL). The resulting mixture was heated to 55° C. and stirred at this temperature. The reaction was monitored by TLC using ethyl acetate as eluent, and showed full conversion after 2 h. The mixture was cooled down to room temperature, and a 5 M solution of HCl in dioxane (4 mL) was carefully added ($CO_2$ evolution). The mixture was stirred at 55° C. for 18 h. The reaction mixture was cooled down to room temperature and diluted with a 5 M aqueous solution of HCl (20 mL) and ethyl acetate (5 mL). The phases were separated. The pH of the aqueous phase was adjusted to 7.0 by addition of a 2 M aqueous solution of sodium hydroxide and extracted with ethyl acetate (2×50 mL). The combined organic phases were dried over anhydrous sodium sulfate, filtered and concentrated at reduced pressure using a rotary evaporator. The residue was purified by flash chromatography on silica gel (50 g) using first a 1:2 mixture of ethyl acetate and cyclohexane and then pure ethyl acetate as eluent. The product fractions were pooled and evaporated to yield the title compound as an off white powder (707 mg, 1.71 mmol, 86% yield).

Example 4b: Preparation of 5-(4,6-dimorpholino-1,3,5-triazin-2-yl)-4-(trifluoromethyl)pyridin-2-amine 1

The preparation described in Example 4b was effected in a modified manner as compared to the procedure described in Example 4a making it possible to avoid the chromatographic purification described therein.

To a suspension of Pd(OAc)2 (0.131 kg, 0.58 mol, 0.04 Eq) in tetrahydrofuran (35 L) was added triphenylphosphine (0.452 kg, 1.72 mol, 0.12 Eq) and the mixture was stirred under inert conditions at 20° C. for 23 min to obtain the catalyst solution. In parallel, a biphasic mixture made of a solution of potassium carbonate (6.047 kg, 43.57 mol, 3.2 Eq) in water (15 L) and N,N-dimethyl-N'-[5-(4,4,5,5-tetramethyl-1,3,2-dioxaborolan-2-yl)-4-(trifluoromethyl)-2-pyridyl]formamidine (5.00 kg, 14.6 mol, 1.07 Eq) and 4-(4-chloro-6-morpholino-1,3,5-triazin-2-yl)morpholine (3.916 kg, 13.7 mol, 1.0 Eq) in tetrahydrofuran (30 L) was heated to 44° C. To the resulting mixture was added the catalyst solution during 10 min and the resulting mixture was heated to 56° C. during 24 min and kept stirring at this temperature for 2 h. The mixture was cooled to 24° C. and the phases were separated. To the organic phase was added 5 N aqueous hydrochloric acid (35 L) over 16 min and the mixture was heated to 54° C. over 2 h and kept stirring at this temperature for 13 h. The mixture was concentrated by 30 L through evaporation under reduced pressure at 55° C. during 1.75 h. To the remaining mixture was added 30 L of 2-methyl-tetrahydrofuran and the mixture was again concentrated by 30 L through evaporation under reduced pressure at 55° C. during 53 min. To the remaining mixture was added 30 L 2-methyl-tetrahydrofuran and the mixture was again concentrated by 30 L through evaporation under reduced pressure at 55° C. during 49 min. The resulting solution was cooled to 27° C. over 57 min and diluted with 2-methyl-tetrahydrofuran (40 L) and water (20 L) and the mixture was stirred at 25° C. for 1 h. Some solid material was removed by filtration. The phases of the filtrate were separated and the aqueous phase was mixed with 2-methyl-tetrahydrofuran (40 L). The pH of the resulting mixture was adjusted to 8 by addition of 4 M aqueous sodium hydroxide (35.7 kg) during 50 min at 20° C. and the pH was stabilized at 8.0 by addition of an 8% aqueous sodium bicarbonate solution (12 kg) and the mixture was stirred for 0.5 h. The phases were separated. The organic phase was heated to 60° C., Si-Thiol (Silicycle 0.59 kg) was added and the mixture was stirred at 60° C. for 1 h. The solids were removed by filtration and the filter cake was washed with 2-methyl-tetrahydrofuran (5 L). To the combined filtrates was added Si-Thiol (Silicycle 0.59 kg) and the mixture was stirred at 60° C. for 1 h. The solids were removed by filtration and the filter cake was washed with 2-methyl-tetrahydrofuran (5 L). To the combined filtrates Si-Thiol (Silicycle 0.59 kg) was added and the mixture was stirred at 60° C. for 1 h. The solids were removed by filtration and the filter cake was washed with 2-methyl-tetrahydrofuran (5 L). The combined filtrates were concentrated by 40 L through evaporation under reduced pressure. To the resulting dark brown solution was added heptane (35 L) at 54° C. during 20 min and the mixture was concentrated by 30 L through evaporation under reduced pressure at 60° C. and the mixture was diluted with heptane (35 L) and the mixture was concentrated again by 25 L through evaporation under reduced pressure at 60° C. The resulting thick suspension was cooled to 25° C. and stirred at this temperature for 14 h. The solid was collected by filtration washed with heptane (15 L) and dried under reduced pressure at 60° C. to yield the crude title compound (5.096 kg 12.39 mol, 90%, purity 99.4% a/a). A second identical run resulted in 5.287 kg (12.85 mol, 94%, purity 99.3% a/a) of the crude title compound. A suspension of 10.305 kg of the crude product in ethanol (72 L) was heated to 75° C. for 20 min. To the resulting thin suspension was added water (72 L) in 5 portions (10 L, 11 L, 11 L, 20 L, 20 L) (a clear solution was obtained after addition of the first two portions). The mixture was concentrated by evaporation under reduced pressure by a volume of 56 L. The resulting thick suspension was cooled to 20° C. and stirred at this temperature for 15 h. The solid was collected by filtration washed twice with a 1:1 mixture of ethanol and water (2×20 L) and dried to constant weight under reduced pressure at 60° C. for 2 days to yield the title compound (9.835 kg, 23.91 mol, 87% overall, purity 99.9% a/a) as off white solid melting at 220° C.

Example 5: Alternative preparation of 5-(4,6-dimorpholino-1,3,5-triazin-2-yl)-4-(trifluoromethyl)pyridin-2-amine 1

In contrast to examples 3 and 4 preparation of compound 1 is carried out without isolation of intermediates starting from N'-[5-bromo-4-(trifluoromethyl)-2-pyridyl]-N,N-dimethyl-formamidine.

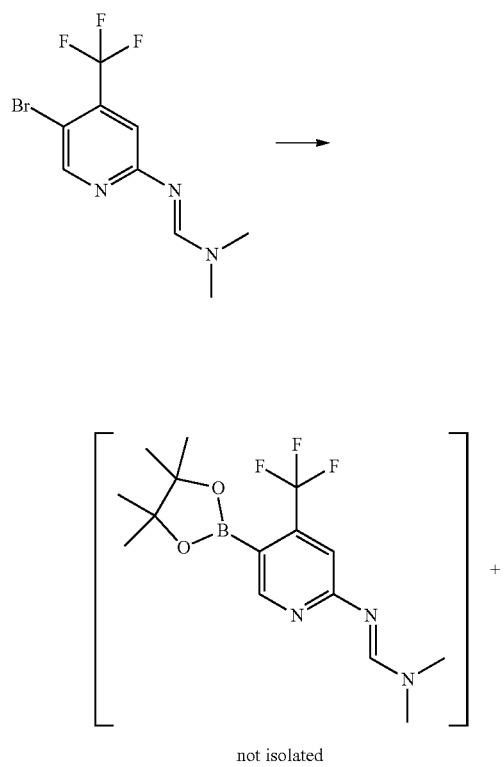

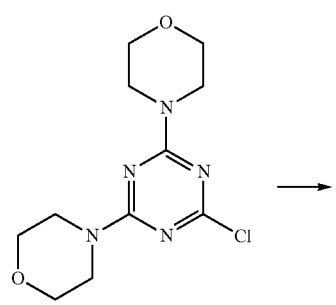

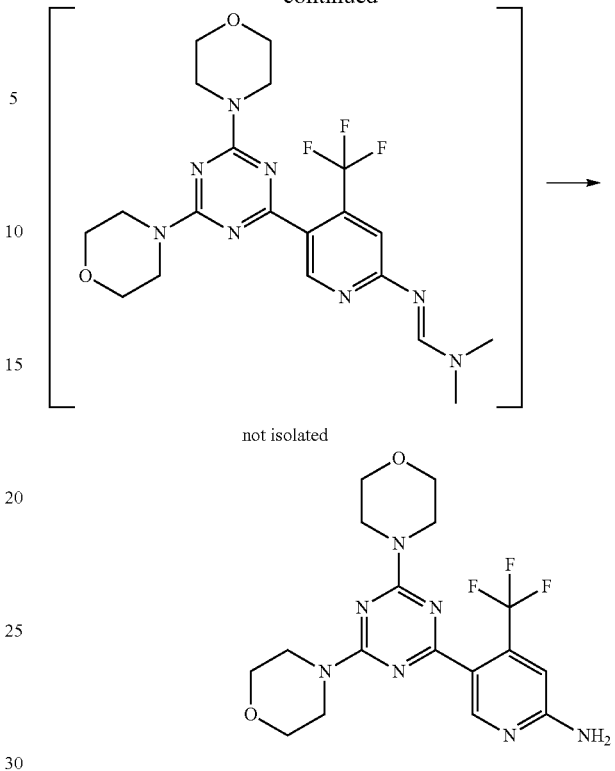

not isolated

To a solution of N'-[5-bromo-4-(trifluoromethyl)-2-pyridyl]-N,N-dimethyl-formamidine (Example 2, 3.40 kg, 11.49 mol, 1 eq) in tetrahydrofuran (24 L) was added dropwise during 1.2 h a 20% solution of isopropylmagnesium chloride in tetrahydrofuran (2.95 L, 13.4 mol, 1.20 eq) at a temperature of 0-4° C. The resulting suspension was stirred at 2° C. for 20 min, then warmed up to 20° C. over a period of 40 min and stirred at this temperature for 7 min. To the resulting suspension was added 2-isopropoxy-4,4,5,5-tetramethyl-1,3,2-dioxaborolane (2.78 kg, 3.00 L, 14.9 mol, 1.3 eq) during 5 min at 20° C. The suspension was then warmed up to 54° C. over a period of 20 min and stirred at this temperature for 1.5 h. The resulting dark brown solution was cooled down to 21° C. during 0.5 h and added to a cold (5° C.) 15% aqueous solution of ammonium chloride (20 L) during 10 min at a temperature not exceeding 15° C. The resulting mixture was stirred for 10 min at 13° C. The phases were separated and the organic phase was washed 3 times with a 13% aqueous solution of sodium chloride (3×34 L). Quantitative analysis by $^1$H NMR of the organic phase revealed 7.3 mol (64% yield) of boronate in 27.3 kg of solution. This solution was stored for 5 days prior to a Suzuki coupling without any degradation as determined by HPLC. For risk reducing purposes the boronate solution was split into two identical runs. To the boronate solution (13.6 kg, 3.64 mol, 1 eq) was added 4-(4-chloro-6-morpholino-1,3,5-triazin-2-yl)morpholine (Example 1, 1.064 kg, 3.73 mol, 1.02 eq) and tetrahydrofuran (3.5 L) and the mixture was warmed up to 40° C. to obtain a homogeneous solution. To this solution was added a solution obtained by mixing palladium acetate (0.051 kg, 0.23 mol, 0.04 eq), triphenylphosphine (0.178 kg, 0.69 mol, 0.12 eq) and tetrahydrofuran (10 L) at 20° C. for 30 min under inert conditions. To the resulting mixture was added a solution of potassium carbonate (2.38 kg, 27.22 mol, 3 eq) in water (5.1 L) and tetrahydrofuran (0.5 L). The resulting mixture was heated to 55° C. during 20 min and stirred at this temperature for 3.5 h. The reaction mixture was cooled down to 24° C. and the phases were separated. To the organic phase was added a 16% aqueous solution of hydrochloric acid (4.6 L), the mixture was heated to 55° C. during 1.3 h and stirred at this temperature for 14 h. The two identical runs (28 L each) were combined for the following work-up procedure. The resulting solution was concentrated by evaporation on a rotary evaporator at 55° C. during 1.5 h. To the resulting solution was added twice 2-methyl-tetrahydrofuran (21 L) followed again by evaporation on a rotary evaporator at 55° C. during 0.75 h. The resulting solution was cooled down to 27° C., mixed with 2-methyl-tetrahydrofuran (27 L) and highly purified water (13 L). The resulting mixture was passed through a pressure filter whereby a small amount of solid was removed and discarded. The phases of the filtrate were separated and the aqueous phase was mixed with 2-methyl-tetrahydrofuran (27 L). The pH of the resulting mixture was adjusted to 8 by dropwise addition of a 4 M solution of sodium hydroxide in water (10 kg) over 1.3 h at 20° C. The phases were separated and the organic phase was heated to 55° C., mixed with Si-Thiol (Silicycle product No R51030B, 0.57 kg) and stirred at 60° C. for 1 h. The hot suspension was filtered and the solids were washed with 2-methyl-tetrahydrofuran (3.5 L). The filtrate was mixed again with fresh Si-Thiol (0.57 kg) and the resulting mixture was stirred at 60° C. for additional 1 h. The resulting solution was concentrated by evaporation of 28 L of solvent under reduced pressure using a rotary evaporator. To the resulting dark brown solution were added heptane isomers (23 L). The resulting suspension was concentrated by evaporation of 23 L of solvent under reduced pressure using a rotary evaporator at 60° C. To the resulting thicker suspension were again added heptane isomers (23 L) and this mixture was again concentrated by evaporation of 23 L of solvent under reduced pressure using a rotary evaporator at 60° C. The resulting thick suspension was diluted with heptane isomers (10 L), the mixture was cooled down to 20° C. and stirred at this temperature for 1 h. The solid was collected by filtration washed with heptane isomers and dried on the rotary evaporator at 60° C. for 1 h to yield the title compound as a brown solid in 98.4% purity (1.977 kg, 4.81 mol, 42%). A suspension of 1.95 kg of this material in ethanol (20 L) was heated to 71° C. during 0.5 h and stirred at this temperature for 20 min. To the resulting suspension was added highly purified water over a period of 20 min. The resulting dark brown solution was concentrated by removing 14 L on the rotary evaporator at 75° C. during 2.5 h. The resulting suspension was cooled down to 20° C. and stirred at this temperature for 15 h. The solid was collected by filtration, washed twice with a mixture of ethanol (3.4 L) and highly purified water (3.4 L) and dried on the rotary evaporator at 60° C. for 24 h to yield the title compound as an off white solid in 99.7% purity (1.683 kg, 4.09 mol, 36% yield) melting at 219-220° C.

TABLE 2

FT-IR major band position assignments for 5-(4,6-dimorpholino-1,3,5-triazin-2-yl)-4-(trifluoromethyl)pyridin-2-amine 1

| Vibration/Functional Group | Wave number (cm$^{-1}$) |
|---|---|
| NH$_2$/H$_2$O | 3444/3333 |
| CH$_2$ | 2905/2854 |
| NH$_2$ | 1636 |
| CH$_2$ | 1485/1385 |

TABLE 2-continued

FT-IR major band position assignments for 5-(4,6-dimorpholino-1,3,5-triazin-2-yl)-4-(trifluoromethyl)pyridin-2-amine 1

| Vibration/Functional Group | Wave number (cm$^{-1}$) |
|---|---|
| C—N | 1428 |
| C—F | 1259 |
| C—O | 1143 |
| C—N | 1106 |
| One isolated aromatic CH | 816 |

$^1$H-NMR (600 MHz, DMSO-d$_6$, δ): 8.62 (s, 1H, o-pyridyl-H), 6.98 (s, 2H, NH$_2$), 6.83 (s, 1H, m-pyridyl-H), 3.76 (m, 8H, morpholine), 3.63 (m, 8H, morpholine).

$^{13}$C-NMR (150 MHz, DMSO-d$_6$, δ): 169.5 (s, triazine), 164.1 (s, triazine), 161.2 (s, o-pyridine), 152.6 (s, o-pyridine), 136.5, 136.2, 136.0, 135.8 (q, p-pyridine), 125.8, 124.0, 122.2, 120.4 (q, CF$_3$), 118.7 (s, m-pyridine), 104.8, 104.7, 104.7, 104.6 (q, m-pyridine), 66.0 (s, morpholine), 43.2 (s, morpholine).

MS (ESI$^+$) m/z: 412.2 [M+H]$^+$. MS (ESI$^-$) m/z: 410.4 [M−H]$^-$ and 456.4 [M+HCOO]$^-$. FT-Raman spectra before and after dynamic vapor sorption (DVS) of 5-(4,6-dimorpholino-1,3,5-triazin-2-yl)-4-(trifluoromethyl)pyridin-2-amine 1 see FIG. 1.

TABLE 3

Comparative yields and properties

| | This invention | WO2010052569 |
|---|---|---|
| Scale | 1.7 kg/9.8 kg | Not determined |
| Yield | 36% (Example 5) | Not determined |
| Yield | 86% (Example 4a) | Not determined |
| Yield | 87% (Example 4b) | Not determined |
| Physical aspect | Off-white solid | Colorless oil |
| Purification technique | Recrystallization | Chromatography |

Example 6: Preparation of 5-(4,6-dimorpholino-1,3,5-triazin-2-yl)-4-(trifluoromethyl)pyridin-2-amine hydrochloride

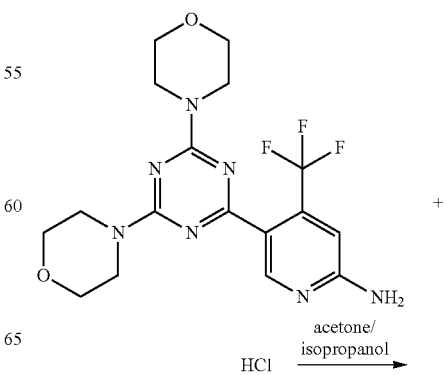

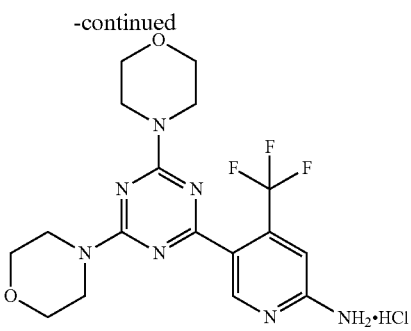

5-(4,6-dimorpholino-1,3,5-triazin-2-yl)-4-(trifluoromethyl)pyridin-2-amine 1 (12 g, 29.2 mmol, 1 eq) was charged into a 1 L round-bottomed flask and dissolved in acetone (400 mL). Then, a 5 M solution of HCl in isopropanol (8.76 mL, 43.8 mmol, 1.5 eq) was added and a white precipitate formed within few minutes. The heterogeneous reaction mixture was stirred for 1 h at room temperature. The resulting suspension was filtered to afford the desired product as a white solid (11.5 g, 88%).

$^1$H NMR (DMSO-d$_6$, 400 MHz, δ): 8.60 (s, 1H), 7.28 (s, 1H), 3.74-3.76 (m, 8H), 3.61-3.64 (m, 8H).

$^{19}$F NMR (DMSO-d$_6$, 376 MHz, δ): −59.3 (s, 3F).

Anal. Calcd for $C_{17}H_{21}ClF_3N_7O_2$: C, 45.59; H, 4.73; N, 21.89. Found: C, 45.49; H, 4.83; N, 21.55.

Example 7a: Preparation of 5-(4,6-dimorpholino-1,3,5-triazin-2-yl)-4-(trifluoromethyl)pyridin-2-amine hydrochloride monohydrate

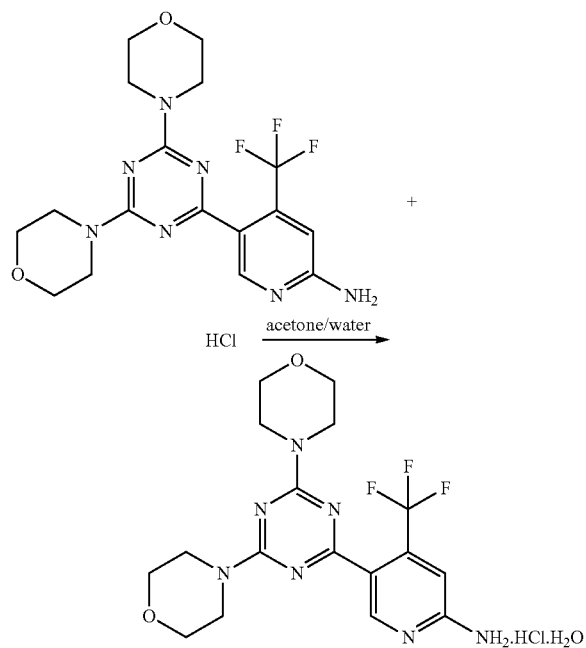

5-(4,6-dimorpholino-1,3,5-triazin-2-yl)-4-(trifluoromethyl)pyridin-2-amine 1 (12 g, 29.2 mmol, 1 eq) was charged into a 1 L round-bottomed flask and dissolved in acetone (400 mL). Then, a 12 M solution of HCl in water (3.65 mL, 43.8 mmol, 1.5 eq) was added and a white precipitate formed within few minutes. The heterogeneous reaction mixture was stirred for 15 h at room temperature. The resulting suspension was filtered to afford the desired product as a white solid (11.4 g, 88%).

$^1$H NMR (DMSO-d$_6$, 400 MHz, δ): 8.59 (s, 1H), 7.21 (s, 1H), 3.74-3.76 (m, 8H), 3.61-3.64 (m, 8H).

$^{19}$F NMR (DMSO-d$_6$, 376 MHz, δ): −59.2 (s, 3F).

Anal. Calcd for $C_{17}H_{23}ClF_3N_7O_3$: C, 43.83; H, 4.98; N, 21.05. Found: C, 43.89; H, 4.83; N, 21.24.

Example 7b: Preparation of 5-(4,6-dimorpholino-1,3,5-triazin-2-yl)-4-(trifluoromethyl)pyridin-2-amine methanesulfonate

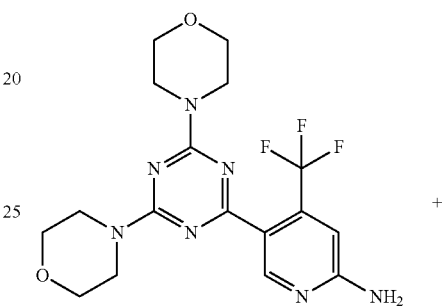

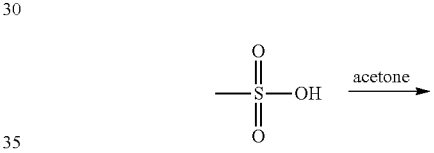

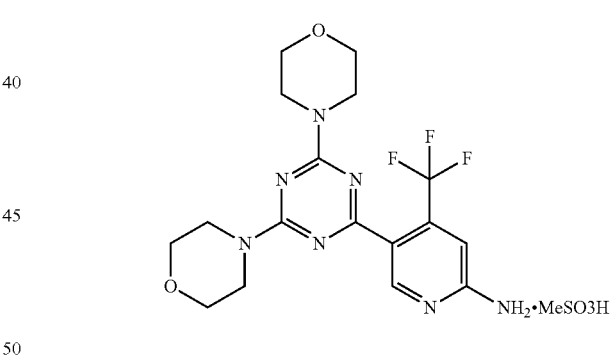

To a solution of 5-(4,6-dimorpholino-1,3,5-triazin-2-yl)-4-(trifluoromethyl)pyridin-2-amine 1 (411 mg, 1 mmol, 1 Eq) in acetone (13.7 mL) was added a solution of methanesulfonic acid (65 μL, 1 mmol, 1 Eq) in acetone (0.65 mL). A white precipitate formed within a few minutes. The heterogeneous reaction mixture was stirred for 16 h at room temperature. The resulting suspension was filtered to afford the title compound as white solid melting at 265° C. (460 mg, 91% yield, purity 99.2% a/a).

$^1$H NMR (DMSO-d$_6$, 400 MHz, δ): 8.58 (s, 1H), 8.50-7.90 (bs, 3H), 7.18 (s, 1H), 3.78-3.73 (m, 8H), 3.65-3.60 (m, 8H), 2.40 (s, 3H).

$^{19}$F NMR (DMSO-d$_6$, 376 MHz, δ): −59.3 (s, 3F).

Anal. Calcd for $C_{18}H_{24}F_3N_7O_5S$: C, 42.51; H, 5.03; N, 20.01. Found: C, 42.60; H, 4.77; N, 19.32.

Example 8: Preparation of 4,4'-(6-chloropyrimidine-2,4-diyl)dimorpholine and 4,4'-(2-chloropyrimidine-4,6-diyl)dimorpholine

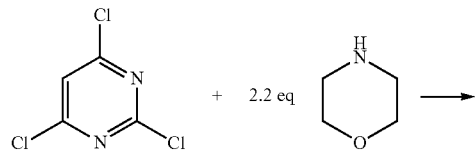

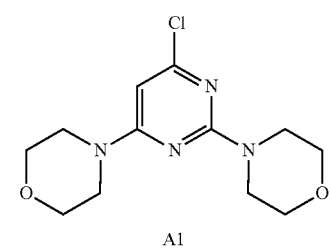

A1

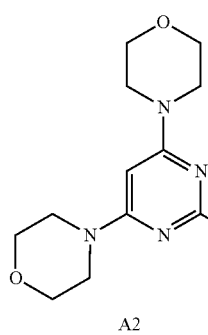

A2

2,4,6-trichloropyrimidine (11.2 g, 61 mmol, 1 eq), N,N-diisopropylethylamine (23.3 mL, 134.2 mmol, 2.2 eq) and morpholine (11.7 mL, 134.2 mmol, 2.2 eq) were charged in a flask and dissolved in ethanol (120 mL). The flask was equipped with a refluxed condenser and placed in an oil bath preheated at 100° C. The reaction mixture was stirred at this temperature for 18 h. After this time, the reaction mixture was cooled down to r.t. and volatiles were removed under reduced pressure using a rotary evaporator. The resulting mixture was dissolved in dichloromethane (100 mL) and washed twice with an aqueous solution of NaHSO$_4$ (2×80 mL). The organic layer was dried over anhydrous sodium sulfate, filtered and concentrated under reduced pressure using a rotary evaporator. Products A1 and A2 were isolated by flash chromatography on silica gel using first a 3:1 mixture of cyclohexane and ethyl acetate and then a 1:1 mixture of cyclohexane and ethyl acetate as eluent. The product fractions were pooled and evaporated to yield A1 as a white powder (13.8 g, 80%) and A2 as a white powder (2.2 g, 13% yield).

4,4'-(6-chloropyrimidine-2,4-diyl)dimorpholine A1

$^1$H NMR (CDCl$_3$, 400 MHz, δ): 5.85 (s, 1H), 3.71-3.75 (m, 12H), 3.52-3.55 (m, 4H). MS m/z: 285.42 [M+H]$^+$.

4,4'(2-chloropyrimidine-4,6-diyl)dimorpholine A2

$^1$H NMR (CDCl$_3$, 400 MHz, δ): 5.38 (s, 1H), 3.73-3.76 (m, 8H), 3.52-3.54 (m, 8H).
MS m/z: 285.24 [M+H]$^+$.

Example 9: Preparation of 5-(2,6-dimorpholinopyrimidin-4-yl)-4-(trifluoromethyl)pyridin-2-amine 2

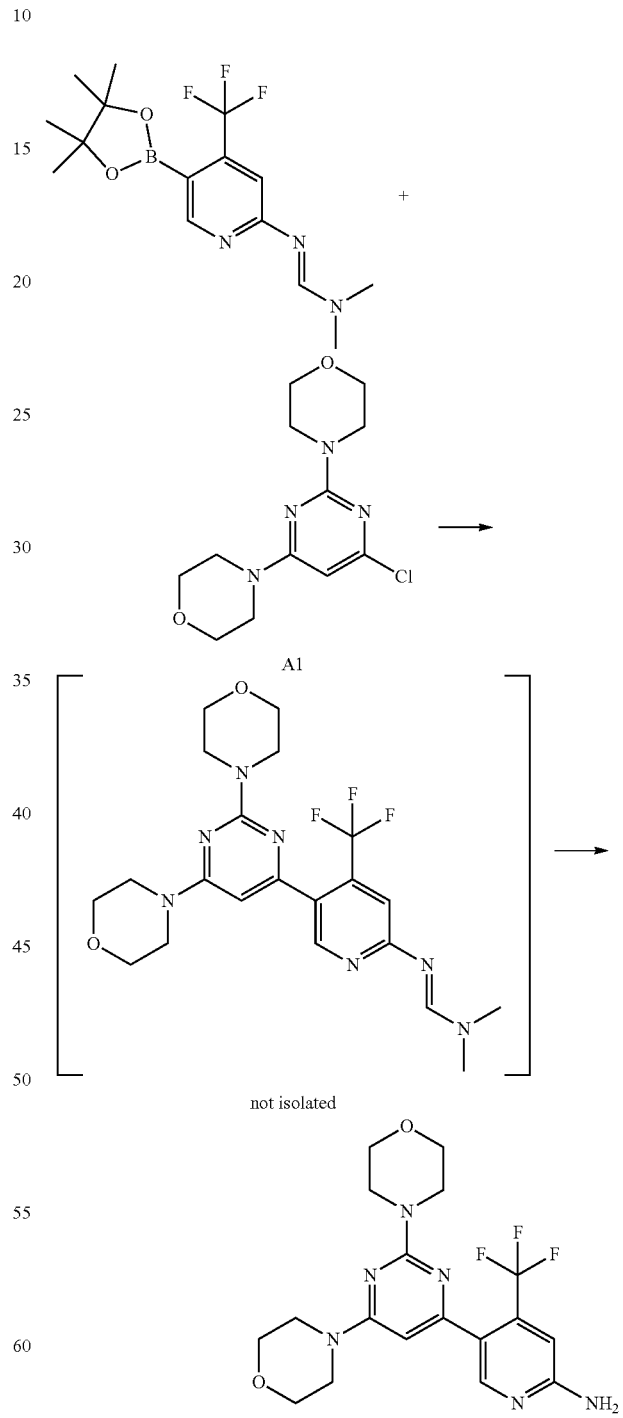

A mixture of palladium acetate (2.2 mg, 0.001 mmol. 0.04 eq) and triphenylphosphine (7.6 mg, 0.03 mmol, 0.12 eq) in tetrahydrofuran (0.8 mL) was stirred at room temperature for 1 h. The resulting solution was added to a flask containing a solution of 4,4'-(6-chloro-pyrimidine-2,4-diyl)dimorpholine (Example 8, 69 mg, 0.24 mmol, 1 eq) and (E)-N,N-dimethyl-N'-(5-(4,4,5,5-tetramethyl-1,3,2-dioxaborolan-2-yl)-4-(trifluoromethyl)pyridin-2-yl)-formamidine (Example 3, 100 mg, 0.29 mmol, 1.2 eq) in tetrahydrofuran (0.6 mL) and a solution of potassium carbonate (101 mg, 0.73 mmol, 3 eq) in water (0.3 mL) and the resulting mixture was heated to 55° C. The reaction was monitored by TLC using ethyl acetate as eluent, and showed full conversion after 2 h. The mixture was cooled down to room temperature, and a 5 M solution of HCl in dioxane (0.5 mL) was carefully added ($CO_2$ evolution), and the mixture was stirred at 55° C. for 18 h. The mixture was cooled down to room temperature and diluted with a 5 M aqueous solution of HCl (2 mL) and ethyl acetate (1 mL). The phases were separated. The pH of the aqueous phase was adjusted to 7.0 by addition of a 2 M aqueous solution of sodium hydroxide and extracted with ethyl acetate (2×10 mL). The combined organic extracts were dried over anhydrous sodium sulfate, filtered and concentrated under reduced pressure using a rotary evaporator. The residue was purified by flash chromatography on silica gel (5 g) using first a 1:2 mixture of ethyl acetate and cyclohexane and then pure ethyl acetate as eluent. The product fractions were pooled and evaporated to yield the title compound as an off white powder (82 mg, 0.2 mmol, 82% yield).

$^1$H NMR (CDCl$_3$, 400 MHz, δ): 8.27 (s, 1H), 6.78 (s, 1H), 5.97 (s, 1H), 4.79 (s, 2H), 3.77 (m, 8H), 3.60 (m, 8H).

$^{19}$F NMR (CDCl$_3$, 376 MHz, δ): −59.7 (s, 3F).

MS m/z: 411.25 [M+H]$^+$.

Example 10: Preparation of 5-(4,6-dimorpholinopyrimidin-2-yl)-4-(trifluoromethyl)pyridin-2-amine 3

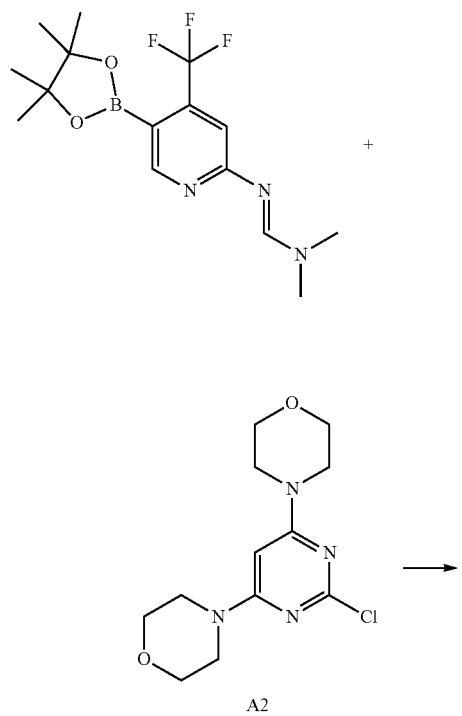

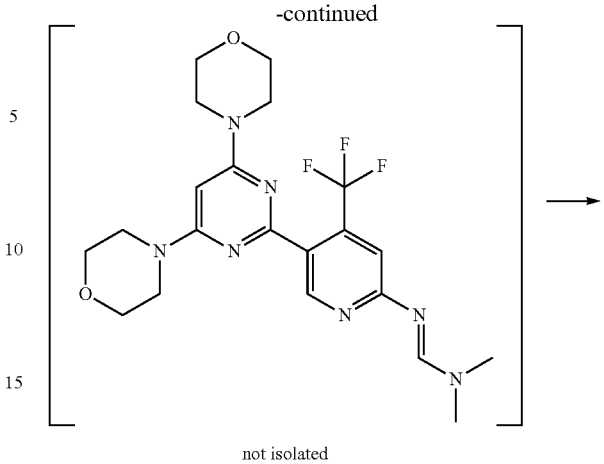

not isolated

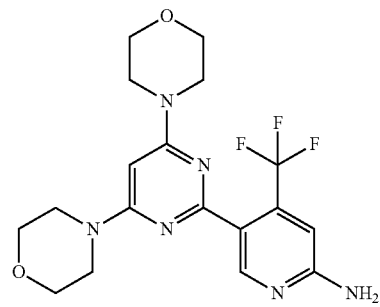

A mixture of palladium acetate (9 mg, 0.04 mmol. 0.04 eq) and triphenylphosphine (31 mg, 0.12 mmol, 0.12 eq) in tetrahydrofuran (3.1 mL) was stirred at room temperature for 1 h. The resulting solution was added to a solution of 4,4'-(2-chloropyrimidine-4,6-diyl)dimorpholine (Example 8, 285 mg, 1 mmol, 1 eq) and (E)-N,N-dimethyl-N'-(5-(4,4,5,5-tetramethyl-1,3,2-dioxaborolan-2-yl)-4-(trifluoromethyl)pyridin-2-yl)formamidine (Exemple 3, 411 mg, 1.2 mmol, 1.2 eq) in tetrahydrofuran (2.5 mL) and a solution of potassium carbonate (414 mg, 3 mmol, 3 eq) in water (1.25 mL) and the resulting mixture was heated to 55° C. The reaction was monitored by TLC using ethyl acetate as eluent, and showed full conversion after 2 h. The mixture was cooled down to room temperature, and a 5 M solution of HCl in dioxane (2 mL) was carefully added ($CO_2$ evolution), and the mixture was stirred at 55° C. for 18 h. The mixture was cooled down to room temperature and diluted with a 5 M aqueous solution of HCl (20 mL) and ethyl acetate (5 mL). The phases were separated. The pH of the aqueous phase was adjusted to 7.0 by addition of a 2 M aqueous solution of sodium hydroxide and extracted with ethyl acetate (2×50 mL). The combined organic extracts were dried over anhydrous sodium sulfate, filtered and concentrated under reduced pressure using a rotary evaporator. The residue was purified by flash chromatography on silica gel (10 g) using first a 1:2 mixture of ethyl acetate and cyclohexane and then pure ethyl acetate as eluent. The product fractions were pooled and evaporated to yield the title compound as an off white powder (235 mg, 0.57 mmol, 57% yield).

¹H NMR (CDCl₃, 400 MHz, δ): 8.86 (s, 1H), 6.77 (s, 1H), 5.51 (s, 1H), 4.78 (s, 2H), 3.78 (m, 8H), 3.59 (m, 8H).

¹⁹F NMR (CDCl₃, 376 MHz, δ): −59.9 (s, 3F).

MS m/z: 411.25 [M+H]⁺.

Example 11: Preparation of 4,4'-(6-chloropyridine-2,4-diyl)dimorpholine and 4,4'44-chloropyridine-2,6-diyl)dimorpholine

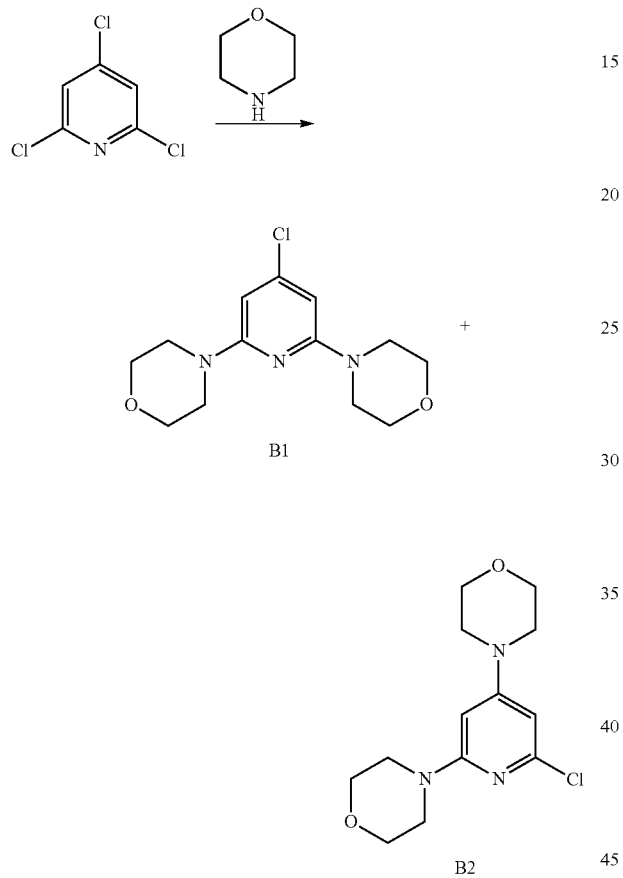

To a mixture of 2,4,6-trichloropyridine (5 g, 27.5 mmol. 1 eq), morpholine (7.2 mL, 82.3 mmol, 3 eq), sodium tert-butoxide (7.9 g, 82.3 mmol, 3 eq), (2-biphenyl)di-tert-butyl-phosphine (408 mg, 2.7 mmol, 0.05 eq) in tetrahydrofuran (80 mL) was added Pd(dppf)Cl₂ (from Combi-blocks, product number: OT-0746), 1 g, 2.7 mmol, 0.05 eq). The mixture was stirred at 80° C. for 4 h. The mixture was cooled down to room temperature and poured onto a saturated solution of NH₄Cl (100 mL). The phases were separated and the aqueous phase was extracted with ethyl acetate (2×100 mL). The combined organic extracts were dried over anhydrous sodium sulfate, filtered and evaporated under reduced pressure using a rotary evaporator. Products B1 and B2 were isolated by flash chromatography on silica gel using first a 1:4.5 mixture of ethyl acetate and cyclohexane and then 1:1 mixture of ethyl acetate and cyclohexane as eluent. The product fractions were pooled and evaporated to yield B1 as an off white powder (2.45 g, 8.6 mmol, 31%) and B2 as an off white powder (2.2 g, 7.8 mmol, 28% yield).

4,4'-(6-chloropyridine-2,4-diyl)dimorpholine) B1

¹H NMR (CDCl₃, 400 MHz, δ): 6.19 (s, 1H), 5.77 (s, 1H), 3.80 (m, 8H), 3.45 (m, 4H), 3.24 (m, 4H).

MS m/z: 283.67 [M+H]⁺.

4,4'-(4-chloropyridine-2,6-diyl)dimorpholine B2

¹H NMR (CDCl₃, 400 MHz, δ): 6.00 (s, 1H), 3.78 (m, 8H), 3.45 (m, 8H).

MS m/z: 283.56 [M+H]⁺.

Example 12: Preparation of 5-(4,6-dimorpholino-2-pyridyl)-4-(trifluoromethyl)pyridin-2-amine 4

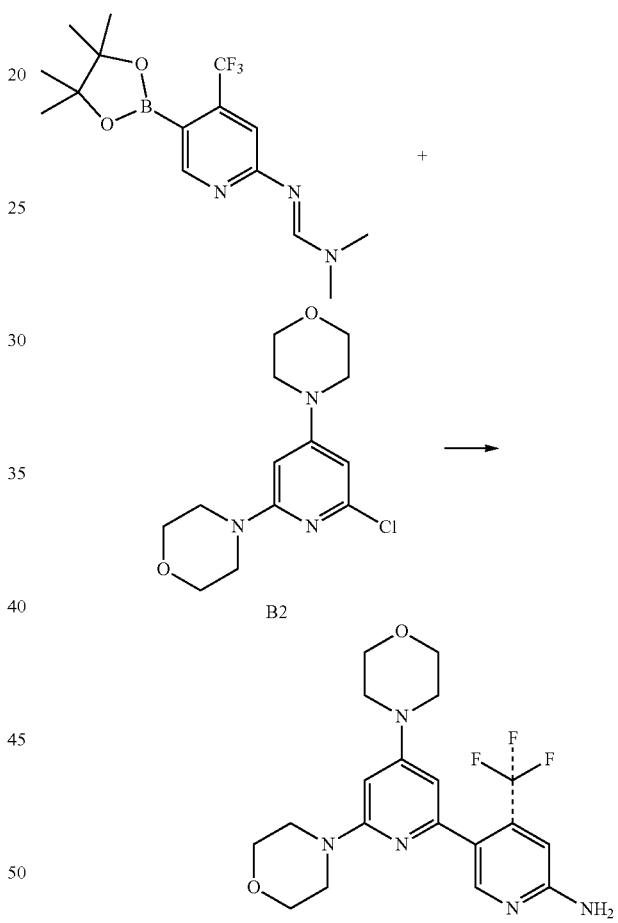

4,4'-(6-Chloropyridine-2,4-diyl)dimorpholine (Example 11, 281 mg, 1 mmol, 1 eq), (E)-N,N-dimethyl-N'-(5-(4,4,5,5-tetramethyl-1,3,2-dioxaborolan-2-yl)-4-(trifluoromethyl) pyridin-2-yl)-formamidine (Example 3, 412 mg, 1.2 mmol, 1.2 eq), tribasic potassium phosphate (424 mg, 2 mmol, 2 eq) and chloro(2-dicyclohexylphosphino-2',4',6'-triisopropyl-1,1'-biphenyl) [2-(2'-amino-1,1'-biphenyl)]-palladium (II) (Sigma-Aldrich (product number: 741825), 39.4 mg, 0.05 mmol, 0.05 eq) were charged in a flask. The vessel was placed under vacuum and then backfilled with nitrogen. The operation was repeated three times, and dioxane (10 mL) was added followed by deionized water (5 mL). The flask was then placed in an oil bath preheated at 100° C. and stirred for 24 h. After this time, the reaction mixture was cooled down to room temperature, quenched with brine (20 mL) and extracted with ethyl acetate (3×40 mL). The organic extracts were dried over anhydrous sodium sulfate, filtered and concentrated to dryness under reduced pressure using a rotary evaporator. The crude mixture was purified by flash chromatography on silica gel (ethyl acetate, $R_f$=0.2) to afford the title compound as a white to pale yellow foam (360 mg, 88% yield).

$^1$H NMR (CDCl$_3$, 400 MHz, δ): 8.26 (s, 1H), 6.77 (s, 1H), 6.31-6.31 (d, J$_{HH}$=1.9 Hz, 1H), 5.93-5.93 (d, J$_{HH}$=1.9 Hz, 1H), 4.73 (brs, 2H), 3.79-3.85 (m, 8H), 3.48-3.51 (m, 4H), 3.26-3.29 (m, 4H).

$^{19}$F NMR (CDCl$_3$, 376 MHz, δ): −59.8 (s, 3F).

MS m/z: 410 [M+H]$^+$.

Example 13: Preparation of 5-(2,6-dimorpholino-4-pyridyl)-4-(trifluoromethyl)pyridin-2-amine 5

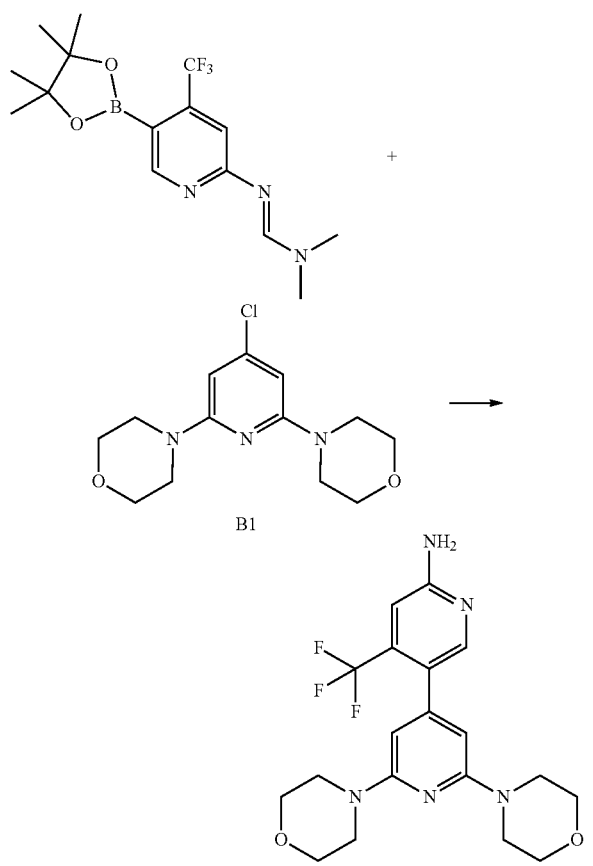

4,4'-(4-Chloropyridine-2,6-diyl)dimorpholine (Example 11, 140.5 mg, 0.5 mmol, 1 eq), (E)-N,N-dimethyl-N'-(5-(4,4,5,5-tetramethyl-1,3,2-dioxaborolan-2-yl)-4-(trifluoromethyl)pyridin-2-yl)formamidine (Example 3, 206 mg, 0.6 mmol, 1.2 eq), tribasic potassium phosphate (212 mg, 1 mmol, 2 eq) and chloro(2-dicyclohexylphosphino-2',4',6'-triisopropyl-1,1'-biphenyl)[2-(2'-amino-1,1'-biphenyl)]-palladium(II) (Sigma-Aldrich (product number: 741825), 19.7 mg, 0.025 mmol, 0.05 eq) were charged in a flask. The vessel was placed under vacuum and then backfilled with nitrogen. The operation was repeated three times, and dioxane (5 mL) was added followed by deionized water (2.5 mL). The flask was then placed in an oil bath preheated at 100° C. and stirred for 24 h. After this time, the reaction mixture was cooled down to room temperature, quenched with brine (10 mL) and extracted with ethyl acetate (3×20 mL). The organic extracts were dried over anhydrous sodium sulfate, filtered and concentrated to dryness under reduced pressure using a rotary evaporator. The crude mixture was purified by flash chromatography on silica gel (cyclohexane/ethyl acetate:1/1, $R_f$=0.2) to afford the title compound as a white to pale yellow foam (166 mg, 81% yield).

$^1$H NMR (CDCl$_3$, 400 MHz, δ): 8.06 (s, 1H), 6.77 (s, 1H), 5.95 (s, 2H), 4.73 (brs, 2H), 3.80-3.82 (m, 8H), 3.47-3.49 (m, 8H).

$^{19}$F NMR (CDCl$_3$, 376 MHz, δ): −59.9 (s, 3F).

MS m/z: 410 [M+H]$^+$.

Example 14: Preparation of 4-(4,6-dichloro-1,3,5-triazin-2-yl)morpholine

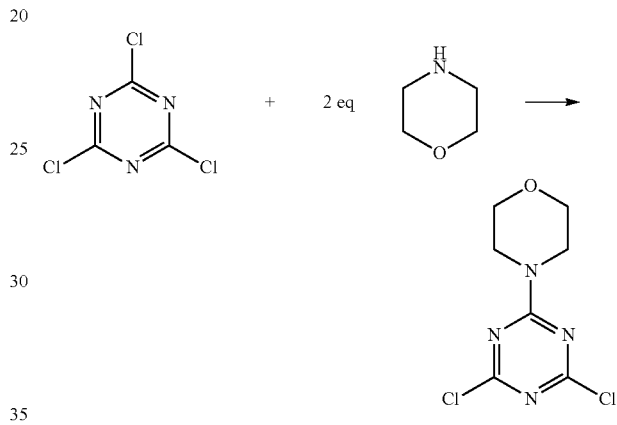

To a solution of cyanuric chloride (10.0 g, 54.2 mmol, 1.0 eq.) in dichloromethane (200 mL) was added morpholine (9.49 mL, 108.4 mmol, 2.0 eq) dropwise at −10° C. The reaction mixture was stirred at this temperature for 6 h, diluted with dichloromethane (200 mL) and mixed with a saturated aqueous solution of NaHSO$_4$ (50 mL). The phases were separated. The organic phase was successively washed with a saturated aqueous solution of NaHSO$_4$ (2×50 mL), dried over anhydrous Na$_2$SO$_4$, filtered and evaporated under reduced pressure to yield pure title compound as a white solid (11.7 g, 92% yield).

$^1$H NMR (CDCl$_3$, 400 MHz, δ): 3.88 (t, J=4.9 Hz, 4H), 3.75 (t, J=4.8 Hz, 4H). MS m/z: 258.6 [M+Na]$^+$.

Example 15: Preparation of (E)-N'-(5-(4-chloro-6-morpholino-1,3,5-triazin-2-yl)-4-(trifluoro-methyl)pyridin-2-yl)-N,N-dimethylformamidine

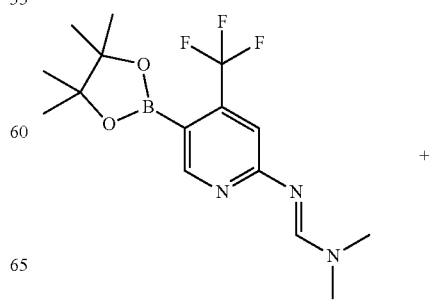

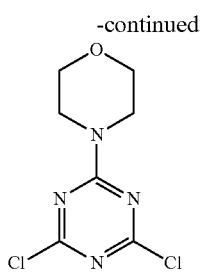

→

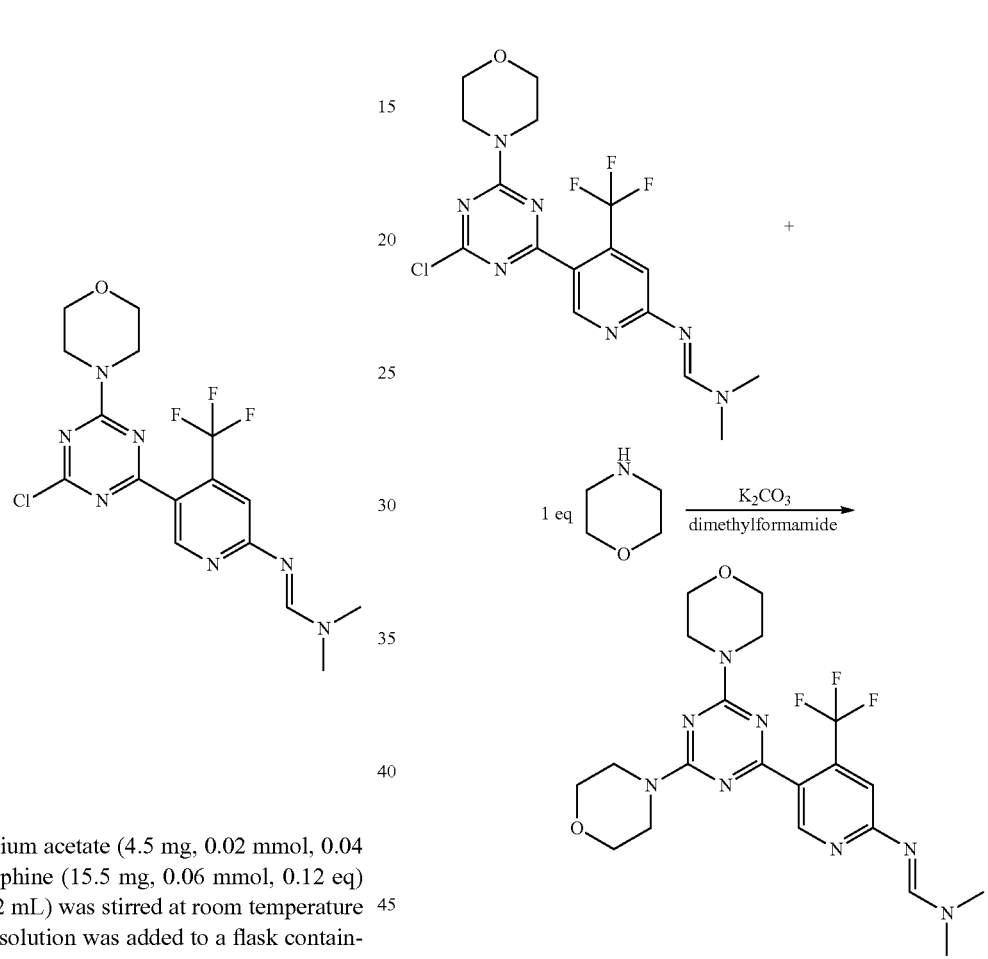

A mixture of palladium acetate (4.5 mg, 0.02 mmol, 0.04 eq) and triphenylphosphine (15.5 mg, 0.06 mmol, 0.12 eq) in tetrahydrofuran (1.2 mL) was stirred at room temperature for 1 h. The resulting solution was added to a flask containing a solution of 4-(4,6-dichloro-1,3,5-triazin-2-yl)morpholine (Example 14, 176 mg, 0.75 mmol, 1.5 eq) and (E)-N,N-dimethyl-N'-(5-(4,4,5,5-tetramethyl-1,3,2-dioxaborolan-2-yl)-4-(trifluoromethyl)-pyridin-2-yl)formamidine (Example 3, 171 mg, 0.5 mmol, 1 eq) in tetrahydrofuran (1 mL) and a solution of potassium carbonate (138 mg, 1 mmol, 2 eq) in water (1 mL), and the resulting mixture was heated to 75° C. The reaction was monitored by TLC using ethyl acetate as eluent, and showed full conversion after 2 h. After this time, the reaction mixture was cooled down to room temperature, quenched with brine (10 mL) and extracted with ethyl acetate (3×20 mL). The organic extracts were dried over anhydrous sodium sulfate, filtered and concentrated to dryness under reduced pressure using a rotary evaporator. The crude mixture was purified by flash chromatography on silica gel (cyclohexane/ethyl acetate 1:3, $R_f$=0.5) to afford the title compound as a white to pale yellow foam (104 mg, 50% yield).

$^1$H NMR (CDCl$_3$, 400 MHz, δ): 8.90 (s, 1H), 8.68 (s, 1H), 7.25 (s, 1H), 3.88 (m, 8H), 3.77 (m, 8H), 3.24 (s, 3H), 3.22 (s, 3H).
$^{19}$F NMR (CDCl$_3$, 376 MHz, δ): −59.8 (s, 3F).
MS m/z: 415.84 [M+H]$^+$.

Example 16: Preparation of (E)-N'-(5-(4,6-dimorpholino-1,3,5-triazin-2-yl)-4-(trifluoromethyl)pyridin-2-yl)-N,N-dimethylformimidamide To a solution of (E)-N'-(5-(4-chloro-6-morpholino-1,3,5-triazin-2-yl)-4-(trifluoro-methyl)pyridin-2-yl)-N,N-dimethylformamidine (Example 15, 207 mg, 0.5 mmol, 1.0 eq.) in dimethylformamide (2 mL) was added morpholine (44 µL, 0.5 mmol, 1 eq) and potassium carbonate (69 mg, 0.5 mmol, 1 eq). The reaction mixture was placed into an oil bath preheated at 70° C. and stirred at this temperature for 15 hr. Then, the reaction mixture was cooled down to room temperature, poured onto a saturated aqueous solution of NH$_4$Cl (75 mL) and extracted with ethyl acetate (2×20 mL). Organic layer was dried over anhydrous Na$_2$SO$_4$, filtered and evaporated under reduced pressure using a rotary evaporator. The residue was purified by flash chromatography on silica gel using first a 1:2 mixture of cyclohexane and ethyl acetate and then a 1:10 mixture of cyclohexane and ethyl acetate as eluent. The product fractions were pooled and evaporated to yield the title compound as a white solid (184 mg, 79% yield).

$^1$H NMR (CDCl$_3$, 400 MHz, δ): 8.81 (s, 1H), 8.56 (s, 1H), 7.23 (s, 1H), 3.84 (brs, 8H), 3.71-3.74 (m, 8H), 3.13 (s, 3H), 3.12 (s, 3H).

$^{19}$F NMR (CDCl$_3$, 376 MHz, δ): −59.7 (s, 3F).

MS m/z: 467.09 [M+H]$^+$.

Example 17: Preparation of 5-(4,6-dimorpholino-1,3,5-triazin-2-yl)-4-(trifluoromethyl)-pyridin-2-amine 1

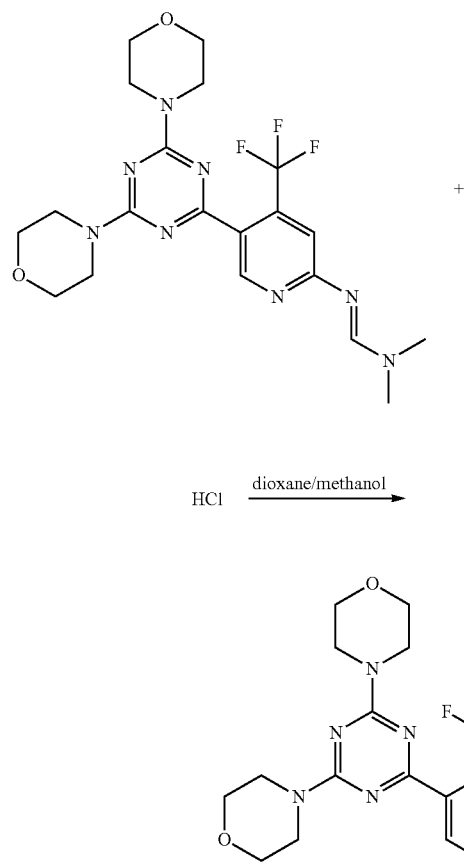

To a solution of (E)-N'-(5-(4,6-dimorpholino-1,3,5-triazin-2-yl)-4-(trifluoromethyl)pyridin-2-yl)-N,N-dimethylformimidamide (Example 16, 121 mg, 0.26 mmol, 1.0 eq.) in methanol (2 mL) was added a 4 M solution of HCl in dioxane (4 mL, 16 mmol, 62 eq). The reaction mixture was placed in an oil bath preheated at 90° C. and stirred at this temperature for 4 h. Then, the reaction mixture was cooled down to room temperature, poured onto a 2 M aqueous solution of NaOH (50 mL) and extracted with ethyl acetate (2×30 mL). The organic layer was dried over anhydrous Na$_2$SO$_4$, filtered and evaporated under reduced pressure using a rotary evaporator. The residue was purified by flash chromatography on silica gel using a 1:3 mixture of cyclohexane and ethyl acetate as eluent. The product fractions were pooled and evaporated to yield the title compound as a white solid (77 mg, 72% yield).

The invention claimed is:

1. A method of manufacturing a compound of formula (I)

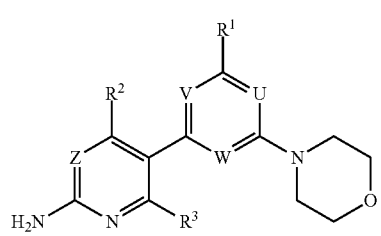

or a stereomer, tautomer or a salt thereof, wherein,

U is CR$^U$ or N, wherein R$^U$ is hydrogen;

V is CR$^V$ or N, wherein R$^V$ is hydrogen;

W is CR$^W$ or N, wherein R$^W$ is hydrogen;

provided that at least one of U, V and W is N;

Z is CR$^Z$ or N, wherein R$^Z$ is hydrogen;

R$^1$ is selected from the group consisting of hydrogen, halogen and —N(R$^T$)R$^S$, wherein R$^T$ and R$^S$ are hydrogen or C$_1$-C$_7$-alkyl, or wherein R$^T$ and R$^S$ together with the nitrogen to which they are attached form a C$_4$-C$_6$ heterocyclic ring selected from the group consisting of

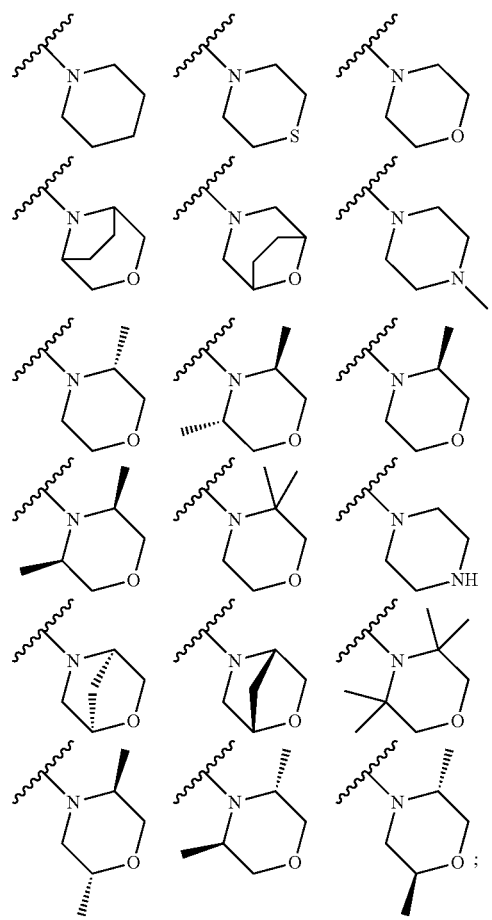

43

$R^2$ is selected from the group consisting of hydrogen, cyano, halogen, methyl and trifluoromethyl; and
$R^3$ is hydrogen or halogen,
comprising reacting a compound of formula (II)

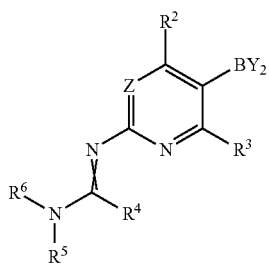
(II)

wherein
$Y_2B$ represents a residue of an acyclic boronic acid, an acyclic boronic ester, or a cyclic boronic ester, and $R^2$ and $R^3$ are defined as for the compound of formula (I);
$R^4$ is hydrogen, $C_1$-$C_7$-alkyl or $C_5$-$C_7$-cycloalkyl;
$R^5$ and $R^6$ are $C_1$-$C_7$-alkyl, or $R^5$ and $R^6$ together represent $C_4$-$C_6$-cycloalkyl:
and the crossed double bond between N and C($R^4$)N indicates a cis and/or trans double bond;
with a compound of formula (III)

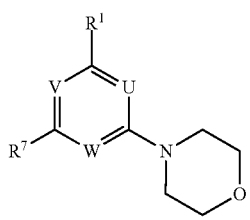
(III)

in which the groups U, V, W and $R^1$ are defined as above; and
$R^7$ is halogen;
in an aqueous organic solvent or an immiscible organic solvent-water mixture at temperatures from 0° C. to the boiling point of the solvent or solvent mixture in the presence of a Pd(0) or Pd(II) phosphine catalyst and a base;
and the resulting formamidine of formula (IV)

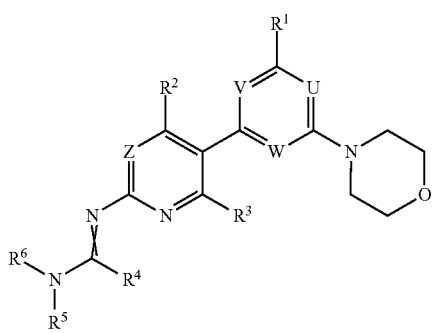
(IV)

44 wherein the substituents have the meanings as defined above,
is hydrolyzed, in situ or after isolation, in aqueous acid or basic solution.

2. The method of claim 1, wherein in the compound of formula (I)
$R^2$ is trifluoromethyl;
and $R^3$ is hydrogen.

3. The method of claim 1, wherein in the compound of formula (II)
$Y_2B$ represents a cyclic boronic ester;
$R^4$ is hydrogen; and
$R^5$ and $R^6$ are methyl.

4. The method of claim 1, wherein the organic solvent is selected from the group consisting of tetrahydrofuran, dioxane and toluene.

5. The method of claim 1, wherein the Pd phosphine catalyst is a mixture of triphenylphosphine and palladium(II) acetate or palladium dichloride.

6. A method of manufacturing a compound of formula (II)

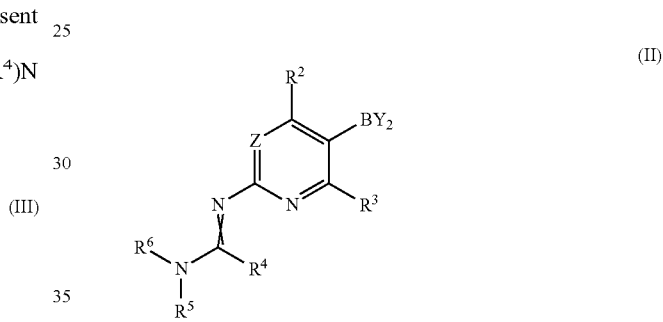
(II)

wherein
$Y_2B$ represents a residue of a boronic acid, an acyclic boronic ester, or a cyclic boronic ester;
Z is $CR^Z$ or N, wherein $R^Z$ is hydrogen;
$R^2$ is selected from the group consisting of hydrogen, cyano, halogen, methyl and trifluoromethyl;
$R^3$ is hydrogen or halogen;
$R^4$ is hydrogen, $C_1$-$C_7$-alkyl or $C_5$-$C_7$-cycloalkyl;
$R^5$ and $R^6$ are $C_1$-$C_7$-alkyl, or $R^5$ and $R^6$ together represent $C_4$-$C_6$-cycloalkyl;
and the crossed double bond between N and C($R^4$)N indicates a cis and/or trans double bond;
comprising treating a compound of formula (V)

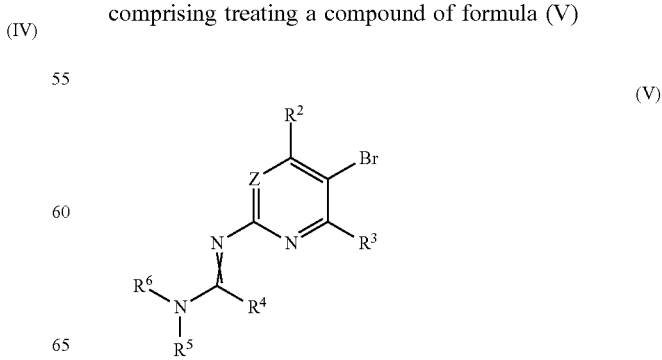
(V)

with an organometallic compound in an organic solvent at temperatures between −80° C. to the boiling point of the solvent and, after completion of the bromine-metal exchange reaction, is further reacted with an organoboron reagent of formula (VI)

$$R^8\text{—}BY_2 \quad (VI)$$

wherein $R^8$ is a leaving group.

7. A method of manufacture of an acid addition salt of formula (Ia)

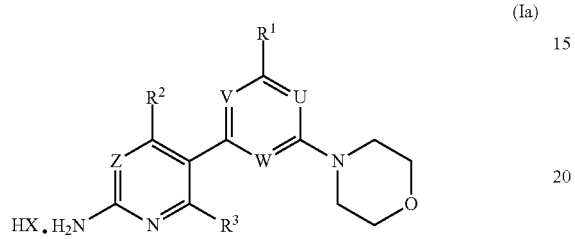

or a stereomer or tautomer, wherein,

U is $CR^U$ or N, wherein $R^U$ is hydrogen;
V is $CR^V$ or N, wherein $R^V$ is hydrogen;
W is $CR^W$ or N, wherein $R^W$ is hydrogen;
provided that at least one of U, V and W is N;
Z is $CR^Z$ or N, wherein $R^Z$ is hydrogen;
$R^1$ is selected from the group consisting of hydrogen, halogen and —N($R^T$)$R^S$, wherein $R^T$ and $R^S$ are hydrogen or $C_1$-$C_7$-alkyl, or wherein $R^T$ and $R^S$ together with the nitrogen to which they are attached form a $C_4$-$C_6$ heterocyclic ring selected from the group consisting of

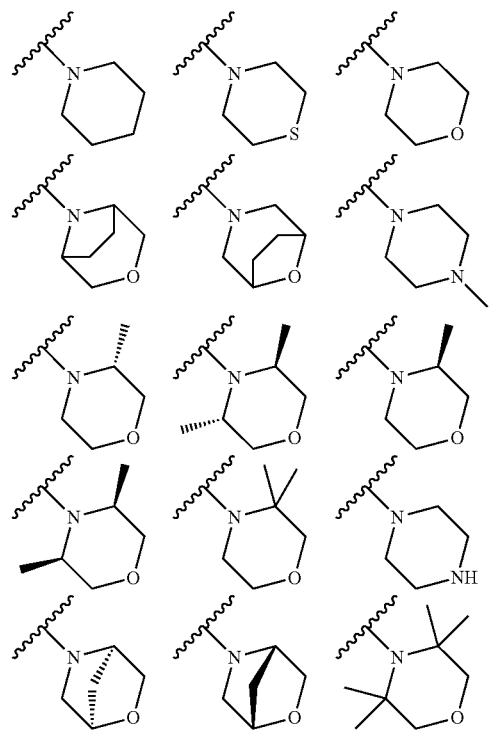

$R^2$ is selected from the group consisting of hydrogen, cyano, halogen, methyl and trifluoromethyl; and
$R^3$ is hydrogen or halogen; and
HX is a protonic acid;
comprising treating a free base of formula (I)

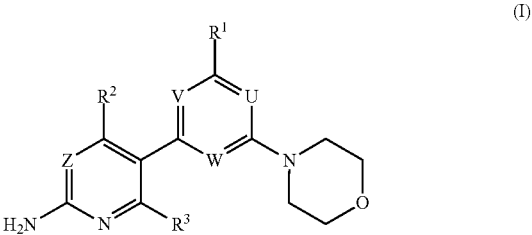

wherein said free base of formula (I) is manufactured according to the method of claim 1; and
wherein the substituents are defined as indicated for formula (Ia),
with protonic acid HX, optionally in a suitable solvent, and the resulting acid addition salt is purified by precipitation from a solvent or recrystallization.

8. The method of claim 1, wherein
$R^1$ is selected from the group consisting of halogen and —N($R^T$)$R^S$, wherein $R^T$ and $R^S$ are, independently of each other, hydrogen, methyl or ethyl, or wherein $R^T$ and $R^S$ together with the nitrogen to which they are attached form a $C_4$-$C_6$-heterocyclic ring selected from the group consisting of

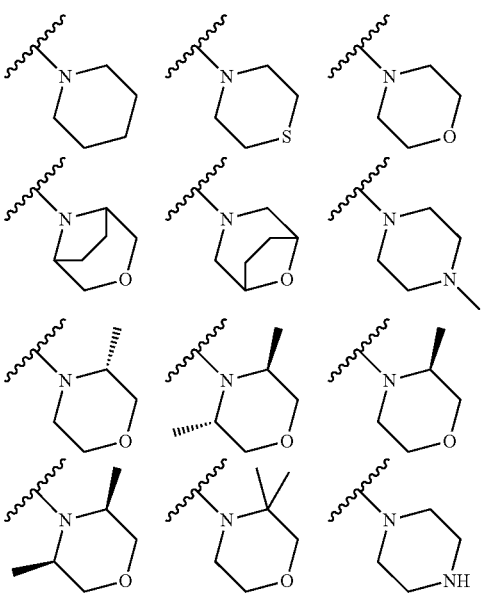

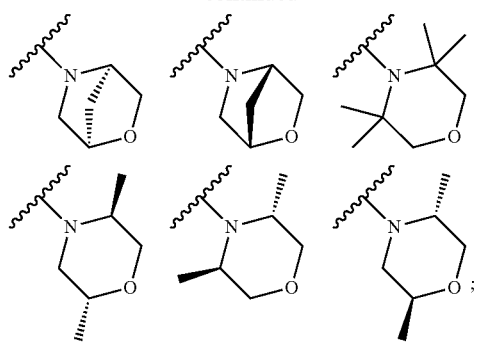

$R^2$ is trifluoromethyl; and
$R^3$ is hydrogen;
and wherein further said resulting formamidine of formula (IV) is reacted with morpholine prior to said its hydrolyzation.

9. The method of claim 1, wherein
$R^1$ is selected from the group consisting of chlorine and —N($R^T$)$R^S$, wherein $R^T$ and $R^S$ are, independently of each other, hydrogen, methyl or ethyl, or wherein $R^T$ and $R^S$ together with the nitrogen to which they are attached form a $C_4$-$C_6$-heterocyclic ring selected from the group consisting of

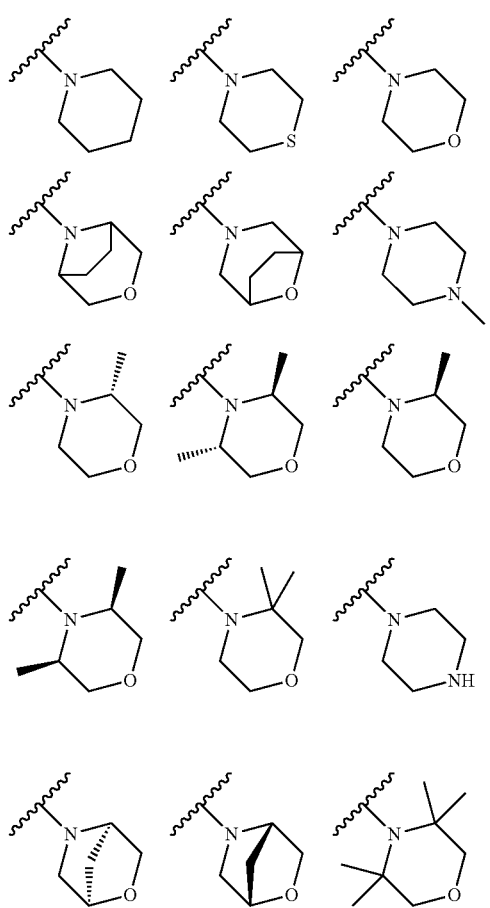

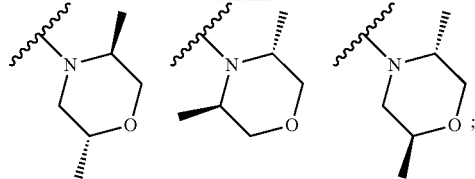

$R^2$ is trifluoromethyl; and
$R^3$ is hydrogen;
and wherein further said resulting formamidine of formula (IV) is reacted with morpholine prior to said its hydrolyzation.

10. The method of claim 1, wherein
U is N; V is N; W is N; Z is $CR^Z$, wherein $R^Z$ is hydrogen;
$R^1$ is selected from the group consisting of halogen and —N($R^T$)$R^S$, wherein $R^T$ and $R^S$ are, independently of each other, hydrogen, methyl or ethyl, or wherein $R^T$ and $R^S$ together with the nitrogen to which they are attached form a $C_4$-$C_6$-heterocyclic ring selected from the group consisting of

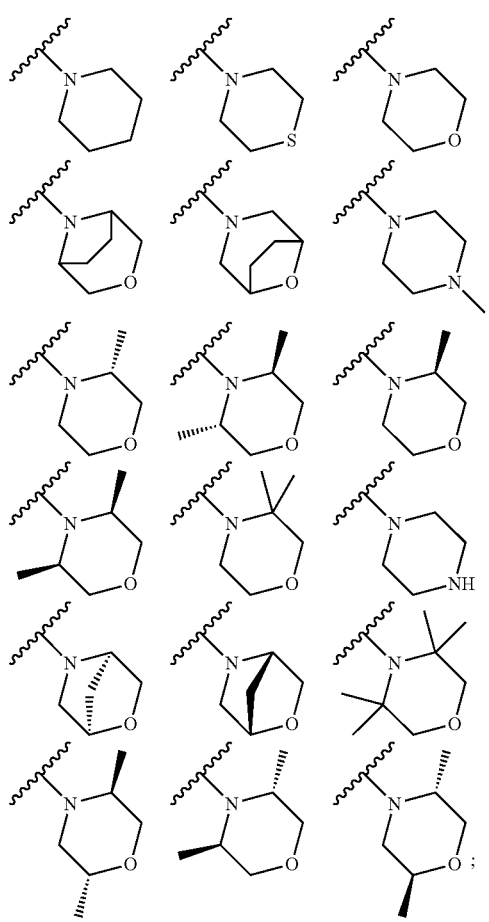

$R^2$ is trifluoromethyl; and
$R^3$ is hydrogen.

11. The method of claim 1, wherein
U is N; V is N; W is N; Z is $CR^Z$, wherein $R^Z$ is hydrogen;
$R^1$ is selected from the group consisting of chlorine and —N($R^T$)$R^S$, wherein $R^T$ and $R^S$ are, independently of each other, hydrogen, methyl or ethyl, or wherein $R^T$ and $R^S$ together with the nitrogen to which they are attached form a $C_4$-$C_6$-heterocyclic ring selected from the group consisting of

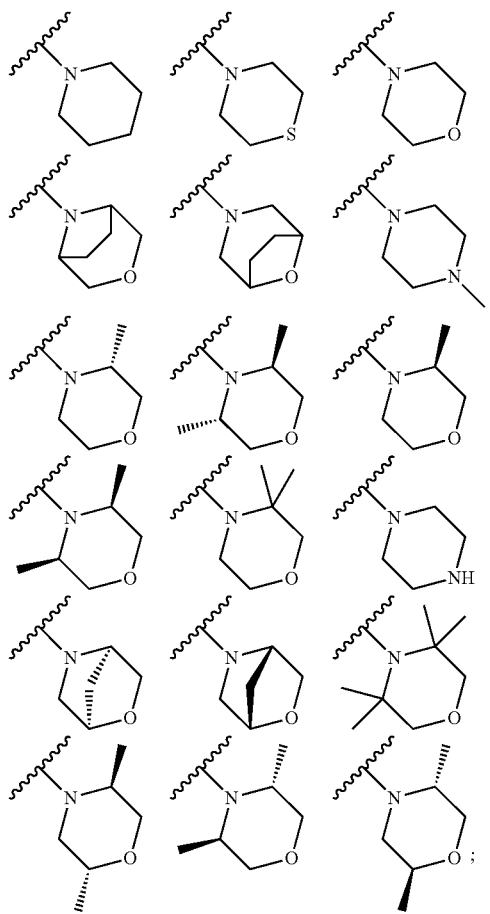

$R^2$ is trifluoromethyl; and
$R^3$ is hydrogen.

12. The method of claim 1, wherein
U is N; V is N; W is N; Z is $CR^Z$, wherein $R^Z$ is hydrogen;
$R^1$ is —$N(R^T)R^S$, wherein $R^T$ and $R^S$ together with the nitrogen to which they are attached form a $C_4$-$C_6$-heterocyclic ring selected from the group consisting of

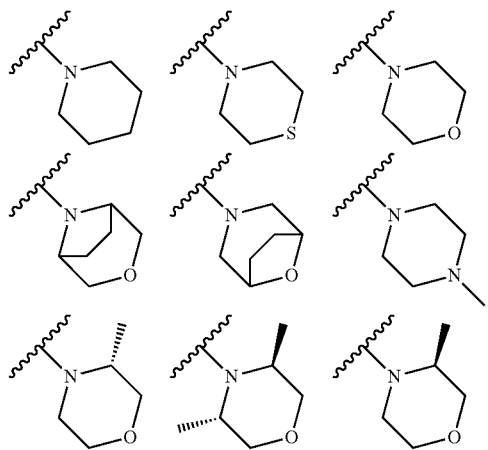

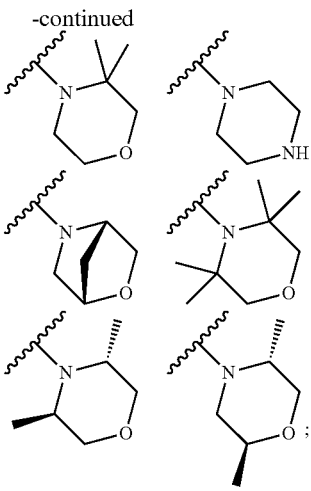

$R^2$ is trifluoromethyl; and
$R^3$ is hydrogen.

13. The method of claim 12, wherein in said compound of formula (II)
$Y_2B$ represents a cyclic boronic ester;
$R^4$ is hydrogen; and
$R^5$ and $R^6$ are methyl.

14. The method of claim 12, wherein said compound of formula (II)
$Y_2B$ represents a pinacolato boronate;
$R^4$ is hydrogen; and
$R^5$ and $R^6$ are methyl.

15. The method of claim 12, wherein in said compound of formula (II)
$Y_2B$ represents a pinacolato boronate;
$R^4$ is hydrogen;
$R^5$ and $R^6$ are methyl; and
$R^7$ is chlorine.

16. The method of manufacture of an acid addition salt of formula (Ia) according to claim 7, wherein
U is N; V is N; W is N; Z is $CR^Z$, wherein $R^Z$ is hydrogen;
$R^1$ is morpholino;
$R^2$ is trifluoromethyl;
$R^3$ is hydrogen; and
the protonic acid HX is selected from hydrochloric acid and methanesulfonic acid.

17. The method of claim 4, wherein
U is N; V is N; W is N; Z is $CR^Z$, wherein $R^Z$ is hydrogen;
$R^1$ is

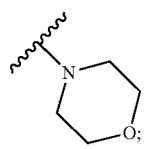 [SMILES: *N1CCOCC1]

$R^2$ is trifluoromethyl; and
$R^3$ is hydrogen.

18. The method of claim 17, wherein said compound of formula (II)
$Y_2B$ represents a pinacolato boronate;
$R^4$ is hydrogen; and
$R^5$ and $R^6$ are methyl.

19. The method of claim 5, wherein
U is N; V is N; W is N; Z is $CR^Z$, wherein $R^Z$ is hydrogen;
$R^1$ is
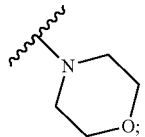 [SMILES: *N1CCOCC1]
$R^2$ is trifluoromethyl; and
$R^3$ is hydrogen.
20. The method of claim 19, wherein said compound of formula (II)
$Y_2B$ represents a pinacolato boronate;
$R^4$ is hydrogen; and
$R^5$ and $R^6$ are methyl.
* * * * *